United States Patent [19]

Fried

[11] 4,309,351
[45] Jan. 5, 1982

[54] CHEMICAL SYNTHESIS
[75] Inventor: Josef Fried, Chicago, Ill.
[73] Assignee: The University of Chicago, Chicago, Ill.
[21] Appl. No.: 118,266
[22] Filed: Feb. 4, 1980

Related U.S. Application Data

[63] Continuation of Ser. No. 967,206, Dec. 7, 1978, abandoned, which is a continuation-in-part of Ser. No. 905,135, May 12, 1978, which is a continuation-in-part of Ser. No. 611,855, Sep. 10, 1975, abandoned, which is a continuation-in-part of Ser. No. 400,297, Sep. 24, 1973, abandoned, which is a continuation of Ser. No. 361,664, May 18, 1973, abandoned, which is a continuation-in-part of Ser. No. 53,663, Jul. 9, 1970, abandoned.

[51] Int. Cl.$^3$ ............................................. C07C 177/00
[52] U.S. Cl. ..................... 260/340.9 P; 260/348.55; 560/123; 562/503; 424/305; 424/317
[58] Field of Search ...................... 260/348.55, 340.9 P

[56] References Cited

PUBLICATIONS

Fried et al. J.A.C.S., 94 4342 (1972).
Fried et al. J. Med. Chem., 16 429 (1973).

Primary Examiner—Robert Gerstl
Attorney, Agent, or Firm—Lawrence Rosen

[57] ABSTRACT

This invention relates to compounds of the formulae

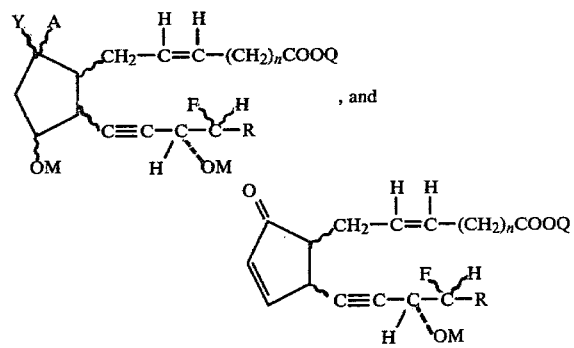

wherein n is an integer from 2 to 5; M is H, acyl, lower alkyl, or lower alkoxy alkyl; Q is H or lower alkyl; R is alkyl, alkenyl or analkyl; A is H; Y is OH, acyloxy or alkoxy, and when taken together, Y and A is oxo (O=), and to novel intermediates therefore.

1 Claim, No Drawings

CHEMICAL SYNTHESIS

The invention described herein was made in the course of work done under a grant or award from the United States Department of Health Education and Welfare.

This application is a continuation application of Ser. No. 967,206 filed Dec. 7, 1978, now abandoned which is a continuation-in-part application of my prior filed copending application Ser. No. 905,135, filed May 12, 1978, which in turn is a continuation-in-part application of my prior filed application Ser. No. 611,855, filed Sept. 10, 1975, now abandoned which in turn is a continuation-in-part application of my prior filed application Ser. No. 400,297, filed Sept. 24, 1973, now abandoned which in turn is a continuation application of prior filed application Ser. No. 361,664, filed May 18, 1973, now abandoned which in turn is a continuation-in-part application of prior filed application, Ser. No. 53,663, filed July 9, 1970, now abandoned.

This invention relates to and has as its objective, the production of pharmacologically active compounds of the formula:

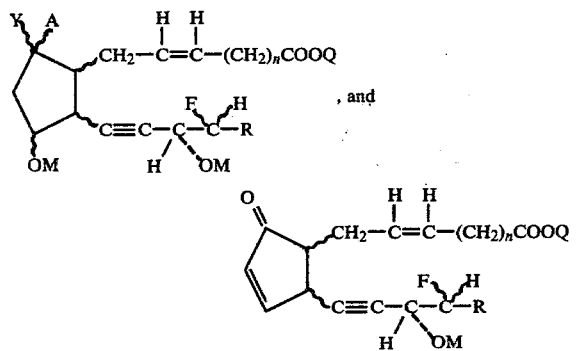

wherein n is an integer of from 2 to 5; M is hydrogen, acyl, lower alkyl, or lower α-alkoxy alkyl; Q is H or lower alkyl; R is alkyl, alkenyl or analkyl; A is hydrogen; Y is hydroxy and when taken together, Y and A is oxo (O=). Preferably, in the practice of this invention, M is hydrogen or methyl; Q is hydrogen or methyl; R is lower alkyl of from 3 to 6 carbon atoms; and n, A, and Y are as hereinabove defined.

[Whenever in the formulae set forth in this Specification and the Claims appended hereto, a curved line ($ ) is employed in the linkage of atoms, it is intended to denote that the connected atom may be either above or below the plane of the paper, as may be determined in each of the respective compounds involved.]

The compounds of this invention are physiologically active compounds which possess prostaglandin-like activity. Thus, the products of this invention may be employed for the purpose of causing the contraction of smooth muscles, as for example, the muscles of the pregnant uterus. Therefore the products of this invention may be employed for the purpose of inducing labor at term or to induce abortion at an earlier stage of pregnancy.

In addition, some of the products of this invention cause regression of the corpus luteum and can therefore be used for estrus synchronization in farm animals so as to achieve greater economy in the practice of artificial insemination.

In addition, some of the products of this invention act as bronchodilators and can therefore be used in the treatment of bronchial asthma, particularly when used in the form of an aerosol. Moreover, these substances are inhibitors of gastric acid and pepsin secretion and can therefore be used in the prevention or treatment of duodenal ulcers.

In addition some of the products of this invention act as hypotensive agents and can therefore be used to treat various hypertensive states.

Some of the products of this invention are inhibitors of platelet aggregation and may therefore be used in the treatment of myocardial infarcts, post-operative thrombosis and atheroschlerosis.

In addition, some of the products of this invention have been found to be resistant to the action of the major prostaglandin inactivating enzyme, prostaglandin 15-dehydrogenase, in fact, they even may serve as inhibitors of this important enzyme. Such failure to be destroyed in the body has the effect of prolonging or enhancing the action of these substances, when compared with the naturally occurring prostaglandins.

The pharmacologically active compounds of this invention may be administered to the mammal being treated therewith in any manner known and convenient to the skilled worker practicing the invention, the dosage and concentration of the final product being adjusted for the requirements of the patient and the properties of the respective compound being employed. The skilled worker may prepare the final products in such compositions and dosage forms as are usually employed for such purposes, depending upon the route of administration selected for the ultimate composition, for example, parenteral, peroral or topical final dosage forms and routes of administration.

Some of the products of this invention are prepared by the processes of this invention which entail a number of steps, beginning with a di-substituted cyclopentyl epoxide as the starting material. The steps involved in the processes of this invention may be generally represented by the following chemical equations wherein R, A, X, V, and $R_1$ are as defined herein:

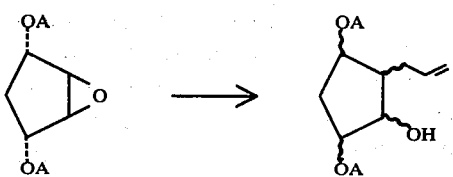

I. A = Benzyl    II (Racemate)

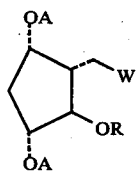   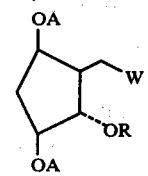

III
a. A = Benzyl; W = C=CH$_2$; R = H
b. A = Benzyl; W = C=CH$_2$; R = Tesyl
c. A = Benzyl; W = 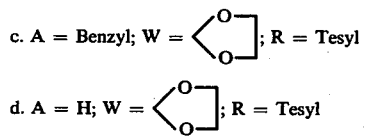; R = Tesyl
d. A = H; W = (same); R = Tesyl IV
a. A = Benzyl; W = C=CH$_2$; R = H
b. A = Benzyl; W = C=CH$_2$; R = Tesyl
c. A = Benzyl; W = (dioxolane); R = Tesyl
d. A = H; W = (dioxolane); R = Tesyl

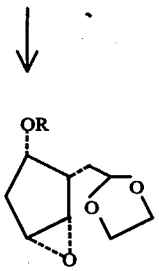   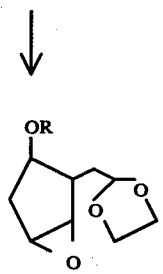

V a. R = H        VI a. R = H

+                  +

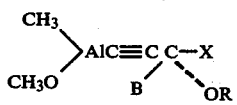

VII
a. X = C$_5$H$_{11}$; R = alkyl; B = H
b. X = CH$_2$—CH=CH—C$_2$H$_5$; R = alkyl; B = H
c. X = CH$_2$—CH=CH—C$_2$H$_5$; R = (CH$_3$)$_3$Si; B = H
d. X = C$_5$H$_{11}$; R = alkyl; B = alkyl

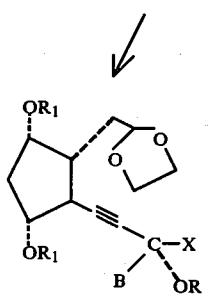   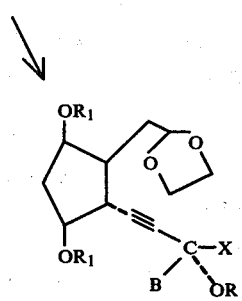

VIII
a. R$_1$ = B = H; R = alkyl; X = C$_5$H$_{11}$
b. R$_1$ = B = H; R = alkyl; x = CH$_2$CHC$_2$H$_5$
c. R$_1$ = H; R = B = alkyl; H; X = C$_5$H$_{11}$ IX
a. R$_1$ = B = H; R = alkyl; X = C$_5$H$_{11}$
b. R$_1$ = B = H; R = alkyl; X = CH$_2$CH=CHC$_2$H$_5$
c. R$_1$ = H; R = B = alkyl; X = C$_5$H$_{11}$ -continued

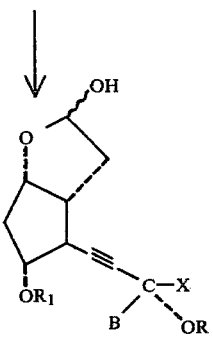

X
a. $R_1 = B = H$; $R =$ alkyl; $X = C_5H_{11}$
b. $R_1 = B = H$; $R =$ alkyl; $X = CH_2CH=CHC_2H_5$
c. $R_1 = H$; $R = B =$ alkyl; $X = C_5H_{11}$

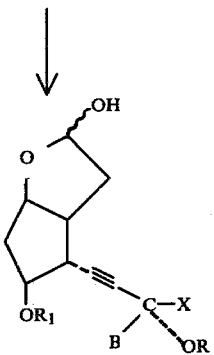

XI
a. $R_1 = B = H$; $R =$ alkyl; $X = C_5H_{11}$
b. $R_1 = B = H$; $R =$ alkyl; $X = CH_2CH=CHC_2H_5$
c. $R_1 = H$; $R = B =$ alkyl; $X = C_5H_{11}$

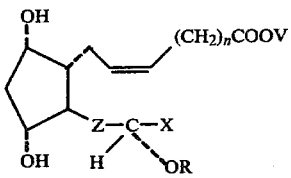

XII
a. $R = H$; $X = C_5H_{11}$; $V = H$; $Z = C\equiv C$
b. $R = H$; $X = C_5H_{11}$; $V =$ alkyl; $Z = C\equiv C$
c. $R = V = H$; $X = CH_2CH=CHC_2H_5$; $Z = C\equiv C$
d. $R = H$; $X = CH_2CH=CHC_2H_5$; $V =$ alkyl; $Z = C\equiv C$
e. $R = V = H$; $X = C_5H_{11}$; $Z =$ cis $C=C$
f. $R = H$; $X = C_5H_{11}$; $V =$ alkyl; $Z =$ cis $C=C$
g. $R = V = H$; $X = CH_2CH=CHC_2H_5$; $Z =$ cis $C=C$
h. $R = H$; $V =$ alkyl; $X = CH_2CH=CHC_2H_5$; $Z =$ cis $C=C$

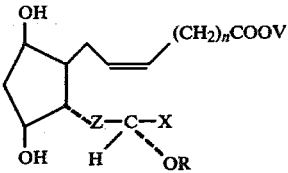

XIII
a. $R = V = H$; $X = C_5H_{11}$; $Z = C\equiv C$
b. $R = H$; $V =$ alkyl; $X = C_5H_{11}$; $Z = C\equiv C$
c. $R = V = H$; $X = CH_2CH=CHC_2H_5$; $Z = C\equiv C$
d. $R = H$; $V =$ alkyl; $X = CH_2CH=CHC_2H_5$; $Z = C\equiv C$
e. $R = V = H$; $X = C_5H_{11}$; $Z =$ cis $C=C$
f. $R = H$; $V =$ alkyl; $X = C_5H_{11}$; $Z =$ cis $C=C$
g. $R = V = H$; $X = CH_2CH=CHC_2H_5$; $Z =$ cis $C=C$
h. $R = H$; $X = CH_2CH=CHC_2H_5$; $V =$ alkyl; $Z =$ cis $C=C$

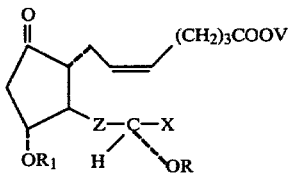

XIV
a. $R_1 = R = V = H$; $X = C_5H_{11}$; $Z = C\equiv C$
b. $R_1 = R = H$; $V =$ alkyl; $X = C_5H_{11}$; $Z = C\equiv C$
c. $R_1 = V = R = H$; $X = CH_2CH=CHC_2H_5$; $Z = C\equiv C$
d. $R = R_1 = H$; $V =$ alkyl; $X = CH_2CH=CHC_2H_5$; $Z = C\equiv C$
e. $R_1 = R = V = H$; $X = C_5H_{11}$; $Z =$ cis $C=C$
f. $R_1 = R = H$; $V =$ alkyl; $X = C_5H_{11}$; $Z = C=C$
g. $R_1 = R = V = H$; $X = CH_2CH=CHC_2H_5$; $Z =$ cis $C=C$
h. $R_1 = R = H$; $V =$ alkyl; $X = CH_2CH=CHC_2H_5$; $Z =$ cis $C=C$

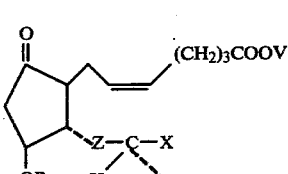

XV
a. $R = R_1 = V = H$; $X = C_5H_{11}$; $Z = C\equiv C$
b. $R = R_1 = H$; $V =$ alkyl; $X = C_5H_{11}$; $Z = C\equiv C$
c. $R = R_1 = V = H$; $X = CH_2CH=CHC_2H_5$; $Z = C\equiv C$
d. $R = R_1 = H$; $V =$ alkyl; $X = CH_2CH=CHC_2H_5$; $Z = C\equiv C$
e. $R = R_1 = V = H$; $X = C_5H_{11}$; $Z =$ cis $C=C$
f. $R = R_1 = H$; $V =$ alkyl; $X = C_5H_{11}$; $Z =$ cis $C=C$
g. $R = R_1 = V = H$; $X = CH_2CH=CHC_2H_5$; $A =$ cis $C=C$
h. $R = R_1 = H$; $V =$ alkyl; $X = CH_2CH=CHC_2H_5$; $Z =$ cis $C=C$

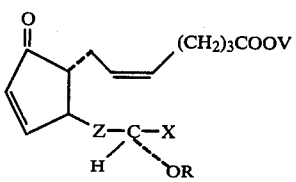

XVI a. V = R = H; X = C₅H₁₁; Z = C≡C
b. R = H; V = alkyl; X = C₅H₁₁; Z = C≡C
c. V = R = H; X = CH₂CH=CHC₂H₅; Z = C≡C
d. R = H; Y = alkyl; X = CH₂CH=CHC₂H₅;
    Z 32 C≡C
e. V = R = H; X = C₅H₁₁; Z = C=C
f. R = H; V = alkyl; X = C₅H₁₁; Z = cis C=C
g. V = R = H; X = CH₂CH=CHC₂H₅; Z = cis C=C
h. V = alkyl; R = H; X = CH₂CH=CHC₂H₅;
    Z = cis C=C -continued

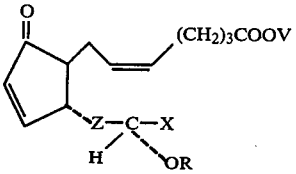

XVII a. V = R = H; X = C₅H₁₁; Z = C≡C
b. R = H; V = alkyl; X = C₅H₁₁; Z = C≡C
c. R = V = H; X = CH₂CH=CHC₂H₅; Z = C≡C
d. R = H; V = alkyl; X = CH₂CH=CHC₂H₅;
    Z = C≡C
e. R = V = H; X = C₅H₁₁; Z = cis C=C
f. R = H; V = alkyl X = C₅H₁₁; Z = cis C=C
g. R = V = H; X = CH₂CH=CHC₂H₅; Z = cis C=C
h. R = H; V = alkyl; X = CH₂CH=CHC₂H₅;
    Z = cis C=C In the first step of the process of this invention, the disubstituted cyclopentyl epoxide (I) is converted, by treatment with lithium allyl cuprate into the allyl derivative (II), as the (±)- racemate. The di-substituted cyclopentyl epoxide (I) starting material may be prepared in accordance with the teachings set forth in my prior filed, copending patent application, Ser. No. 274,365, filed July 24, 1972. The (±)- racemate obtained above, is incapable of being further employed in the practice of this invention. I have found that in order to successfully practice the instant invention and the processes involved therewith, it is essential that only the optically active antipodes of the racemic materials involved can be employed to obtain the desired final products of this invention. It is absolutely necessary therefore, that the racemate (II), be resolved into its optically active antipodes, which after their respective isolation may individually be employed in the processes of this invention to obtain the desired pharacologically active final products of this invention.

Thus, in the case of the resolution of the (±)- allyl derivative racemate (II), the following procedure, as illustrated by the following chemical equations, may be employed:

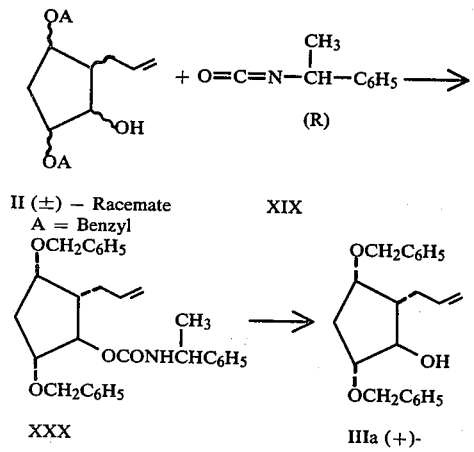

The (±)- racemate (II) is resolved into its optically active antipodes (i.e. Compounds IIIa and IVa) by first converting the racemate into the phenyl urethane derivative, and more particularly the α-phenethyl urethane derivative (XXX) by treatment with an optically active α-phenethyl isocyanate (XIX). More particularly, to obtain the (+)- antipode (IIIa), the (±)- racemate is treated with (+)-(R)-αphenethyl isocyanate to yield the easily crystallizable urethane derivative (XXX), which is then reduced, as by treatment with a reducing agent, for example, lithium aluminum hydride, to yield the optically active (+)- antipode (IIIa). The thus obtained optically active (+)- antipode is then employed in the further practice of the instant invention. Likewise, the same general procedure is employed to obtain the (−)-enantiomer (IVa), except that an equivalent amount of (−)-(S)-α-phenethyl isocyanate is substituted for the (+)-(R)-α-phenethyl isocyanate, thus yielding the (−)-αphenethyl urethane intermediate, which is then reduced to yield the desired optically active (−)- antipode (IVa).

These resultant optically active antipodes may then be further treated in accordance with this invention to yield the desired physiologically active final products. Thus, the respective optically active antipode (IIIa or IVa) is first converted into its tosylate by treatment with toluenesulfonyl chloride in the presence of a base, for example, pyridine. The resultant tosylates (IIIb and IVb), are then subjected to ozonolysis, followed by the reductive cleavage of the ozonide with a reducing agent, for example, zinc and acetic acid, with immediate ketalization of the resultant aldehyde by treatment with ethylene glycol in the presence of an acid catalyst, to yield the resultant ethylene ketal compounds (IIIc and IVc). These ethylene ketal compounds are then reductively debenzylated, as by treatment with palladium on charcoal and hydrogen, followed by treatment of the resultant diol compounds (IIId and IVd), with a base, for example, sodium or potassium hydroxide, to yield the respective oxide derivatives (Va and VIa).

These epoxide derivatives may then be reacted with an aluminum acetylide (VII), to yield the various acetylenic derivatives of this invention (VIII and IX). I have found that most satisfactory results are obtained in the practice of this invention, when the aluminum acetylide employed is one that may be generally characterized as an alkyl-alkoxy-aluminum acetylide, and most preferably, a lower alkyl-lower alkoxy-aluminum acetylide, for example, methyl-methoxy-aluminum acetylide. I have found that the employment of the preferred alkyl-alkoxy-aluminum acetylide in the practice of this invention results in substantial improvement in the yields of the desired final products, over that which may be obtained by employment of other aluminum acetylides, although the use of such other aluminum acetylides will still provide the final products of this invention.

The side chain of the aluminum acetylide employed in the practice of this invention, i.e. in Compounds VII, R and X may be variously substituted to provide the respectively substituted final products of this invention. Thus, where the side chain of the aluminum acetylide is alkyl or alkenyl, i.e. X is alkyl or alkenyl, the side chain is imparted to the compounds produced by the further practice of the process of this invention. Likewise, the various other substituents of the desired final products of of this invention may be obtained by the employment of the properly substituted aluminum acetylide. For example, in Compound VII, where B is hydrogen or lower alkyl, for instance, methyl, and where R is alkyl, and X is alkyl or alkenyl, the respectively substituted acetylenic derivatives (VIII and IX) may be obtained.

The resultant acetylenic compounds (VIII and IX) may then be subjected to mild acid hydrolysis to yield the respective hemi-acetal derivatives (X and XI), which are then subjected to a Wittig reaction by treatment with the ylid derived from 5-triphenyl-phosphoni-ovaleric acid, to yield the desired final products of this invention, (XII and XIII). These final products may then be further treated to yield additional final products of this invention. Thus, the diol final products, (XII and XIII) may be treated with N-trimethylsilyldiethylamine at low temperature, followed by oxidation with an oxidizing agent, for example, chromium trioxide-pyridine complex, followed by desilylation, to yield the desired ketone final products of this invention (XIV and XV).

Further, the acetylenic final products of this invention, (i.e. XII and XIII, wherein Z=C≡C), may be further treated to yield additional final products of this invention. These acetylenic compounds may thus be reduced by treatment with a reducing agent, for example, a Lindlar-catalyst in pyridine, to furnish the desired cis- double bonded final products of this invention, (i.e. Compounds XII and XIII, wherein Z=cis-C=C).

Additional final products of this invention may also be obtained by dehydration of the acetylenic final products of this invention (i.e. wherein Z=C≡C), as for example, by treatment with an acid catalyst, such as a mineral acid, for example, hydrochloric acid, to yield additional unsaturated final products of this invention, (XVI and XVII), which are also new final products of this invention.

In addition to the foregoing, an alternate process for the production of the novel and desired final products of this invention has also been discovered. This alternative process may be generally illustrated by the following chemical equations, wherein A, X, B and R are as defined herein:

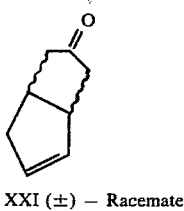

XXI (±) — Racemate

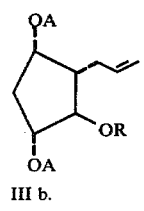

III b.

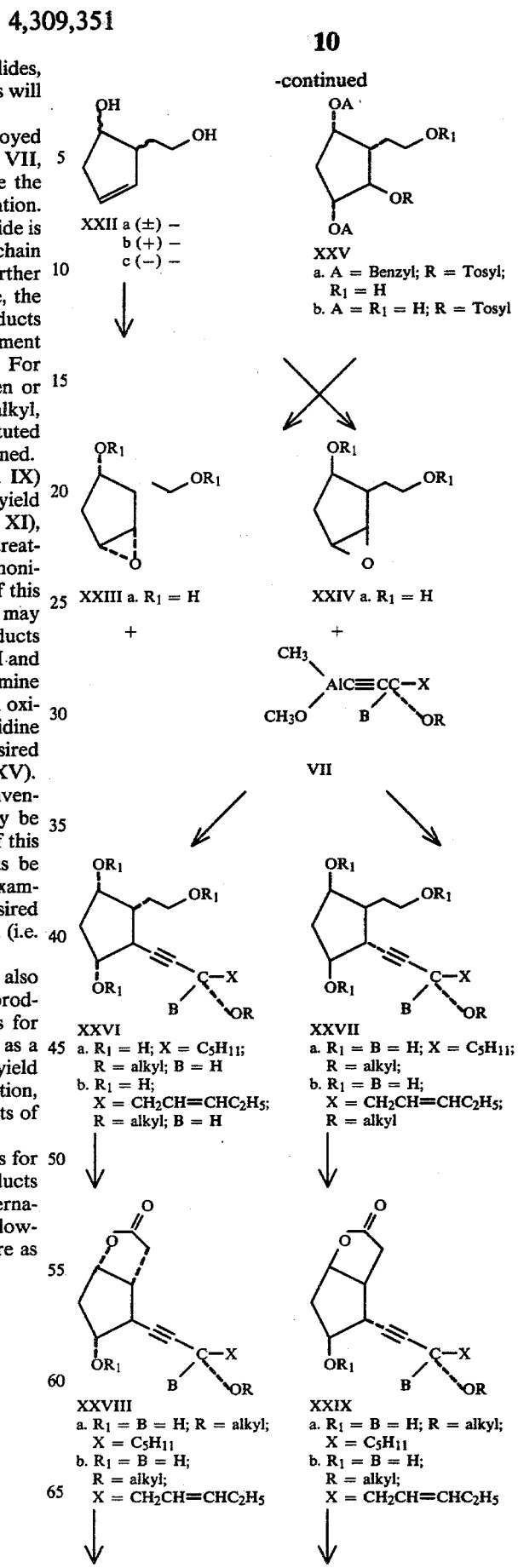

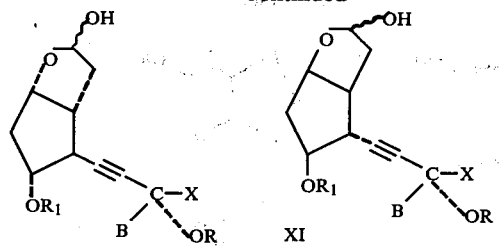

X
a. $R_1 = H$; $R$ = alkyl;
 $X = C_5H_{11}$
b. $R_1 = B = H$; $R$ = alkyl;
 $X = CH_2CH=CHC_2H_5$
c. $R_1 = H$; $R = B$ = alkyl;
 $X = C_5H_{11}$ XI
a. $R_1 = B = H$; $R$ = alkyl;
 $X = C_5H_{11}$
b. $R_1 = B = H$; $R$ = alkyl;
 $X = CH_2CH=CHC_2H_5$
c. $R_1 = H$; $R = B$ = alkyl;
 $X = C_5H_{11}$ In this alternate process, the tosylate (IIIb) is first converted into the primary alcohol (XXVa) by ozonolysis, followed by reduction of the resultant ozonide, by treatment with a reducing agent, for example, sodium borohydride. Then, catalytic debenzylation, by treatment for example, with palladium on charcoal, furnishes the triol tosylate (XXVb), which is then in turn converted into the epoxy diol intermediate (XXIII). The resultant epoxy diol (XXIII) may then be treated with the aluminum acetylide (VII) to yield the triol compounds (XXVI), which are also new products of the instant invention. These triols may then be converted, for example, by selective catalytic oxidation, as by treatment with platinum and oxygen, into the lacton intermediates (XXVIII), which are also new products of the instant invention. These lactones are then converted, as by reduction with a suitable reducing agent, for example, diisobutyl aluminum hydride, to the hemi-acetal compounds (X), which are further thereafter treated to yield the desired final products of this invention by the processes heretofore set forth above.

In a parallel series of reactions, compound IVb is converted via the compounds XXIVa, XXVII, XXIX and XI into further final products of this invention by the processes heretofore set forth above.

In addition to the foregoing, the desired diol epoxide compounds (XXIII and XXIV), may be prepared by first reducing the racemic lactone (±)-XXI, as by treatment with a suitable reducing agent for example, lithium aluminum hydride, to yield the unsaturated diol intermediate (XXII). Since, as hereinbefore set forth, the successful practice of the instant invention requires the use of only the optically active intermediates, the optically active antipodes of the racemic diol (XXIIa), must first be obtained before the process may be practiced. The optical resolution of the unsaturated diol (XXIIa) can be accomplished by the method represented by the following chemical equations:

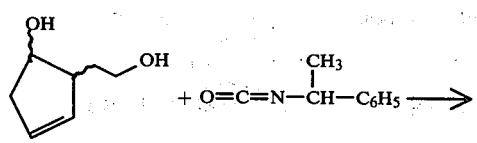

XXIIa (±)—

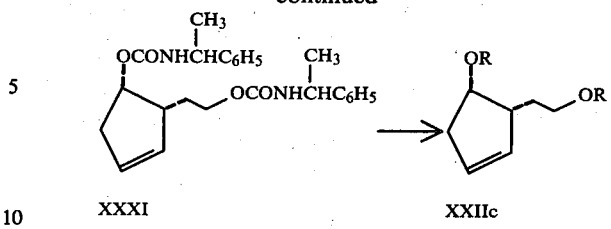

XXXI  XXIIc

Thus, the racemic diol is first reacted with an optically active aralkyl isocyanate, for example, (+)-(R)-α-phenethyl isocyanate, to yield the resultant diurethane intermediate (XXXI), which may then be reduced, as by treatment with lithium aluminum hydride to yield the unsaturated diol (XXIIc), which is also a new product of this invention. The (+)-unsaturated diol may likewise be obtained by following the same general procedure, but substituting an equivalent amount of (−)-(S)-α-phenethyl isocyanate for the (+)-(R)-α-phenethyl isocyanate, as set forth hereinabove.

The respective optically active unsaturated diol antipodes (XXIIb and XXIIc), may then be converted into the desired diol epoxides (XXIII and XXIV), by treatment with m-chloroperbenzoic acid. The resultant epoxides may then be treated in accordance with the procedures set forth hereinabove to yield the desired final products of this invention.

As hereinabove described, the final and intermediate compounds of the instant invention may be variously substituted at certain positions in the molecule of the respective compound involved. For example, those compounds of the instant invention wherein certain substituents thereof are free hydroxyl groups may be acylated to yield the corresponding acylated derivatives thereof. The acylated derivatives may be prepared in the manner generally employed and known by the worker skilled in the art to be useful for such purposes, and may be accomplished by employment of a hydrocarbon carboxylic acid halide, for example, a chloride or anhydride, of less than 12 carbon atoms, including those derived from such carboxylic acids as, alkanoic acids, alkenoic acids, monocyclic aryl acids, cycloalkane acids, and other like acids, as is generally well known to the skilled worker.

Further to the foregoing, it is also contemplated in the practice of this invention, that the free hydroxy groups which may occur in the compounds of this invention, may be further substituted, as for example, by alkylation, as by treatment with a suitable alkylating agent, for instance, sodium hydride and an alkyl iodie, to yield the respective alkoxy substituted compounds of the instant invention. The alkoxy derivatives preferred in the practice of the instant invention include those of lower alkyl substitutions, preferably less than 7 carbon atoms, for example, methyl, ethyl or propyl.

The final products of this invention are prepared by the processes of this invention which entail a number of steps beginning with an epoxy diol compound as the starting material. The steps and processes of this invention may be generally represented by the following chemical equations wherein R and M are as defined hereinafter:

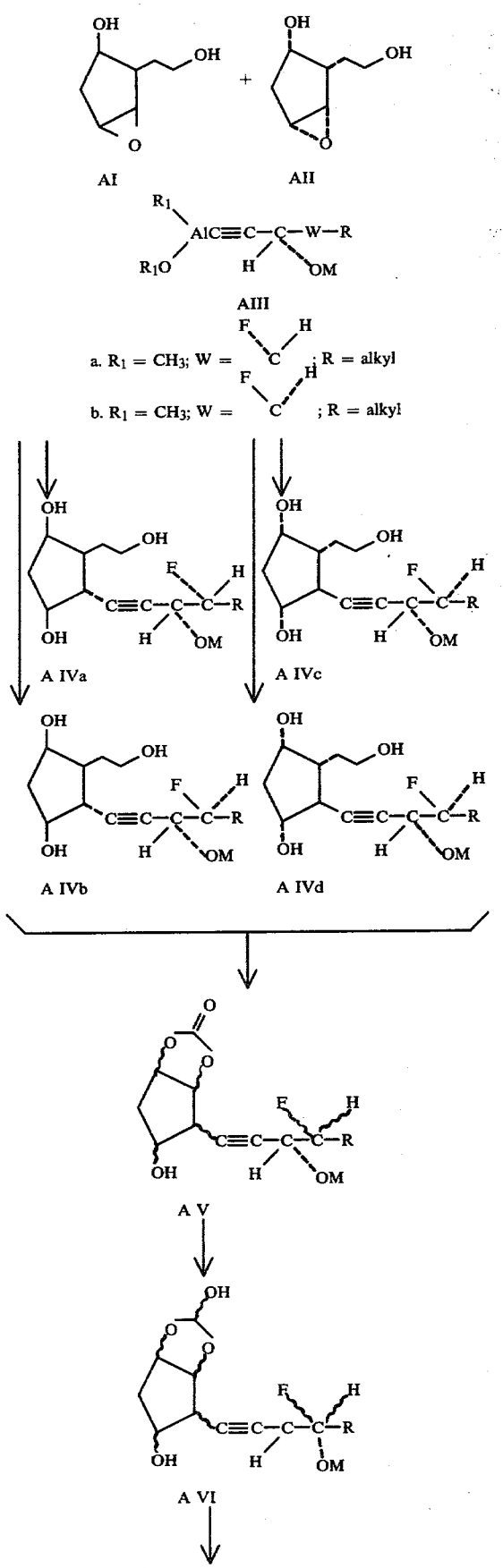

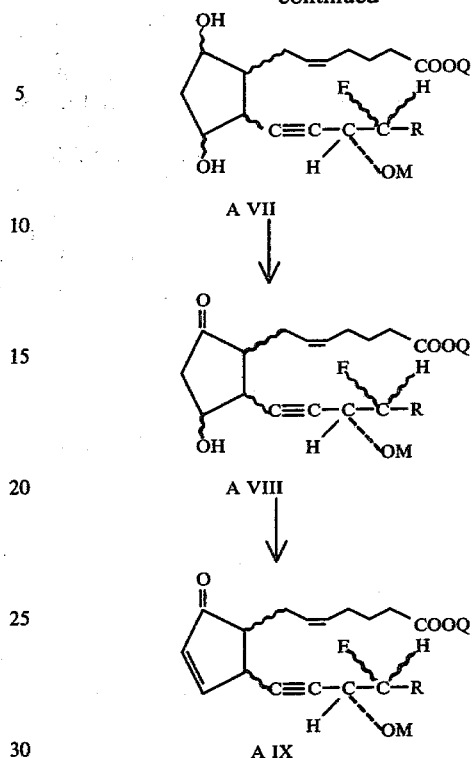

The epoxy diol starting materials of this invention may be prepared in accordance with the teachings of my prior filed Application Ser. No. 400,297, filed Sept. 24, 1973, wherein the method for preparing the epoxy diol starting materials (Compounds XXIII and XXIV) of this invention are disclosed. The epoxy diol compounds are treated with a fluorinated aluminum acetylide (Compounds AIII) to yield the respective halogenated triol compounds (Compounds AIV) of this invention, which are new compounds of this invention.

These triol compounds (Compounds AIV) may then be treated according to the processes of this invention to yield the desired final products thereof. Each of the four stereo isomers of the triol compounds (Compounds AIV a–d) may then be subsequently subjected to the further steps of the process of this invention as represented by the foregoing equations to yield the desired stereoisomeric final products of this invention.

Thus, the halogenated triols (Compounds AIV) are converted to the lactone intermediates, (Compounds AV) as by selective oxidation by treatment with platinum and oxygen. These lactone intermediates are also new compounds of this invention.

The lactone intermediates (Compounds AV) may then be treated with a reducing agent, for example, diisobutyl aluminum hydride to yield the hemiacetal compounds (Compounds AVI) which are also new compounds of this invention.

The hemiacetal intermediates (Compounds AVI) may then be subjected to a Wittig reaction as by treatment with the ylid derived from 5-triphenyl phosphoniovaleric acid, followed by dealkylation, e.g., debutylation, with trifluoroacetic acid to yield the dihydroxy final products of this invention (Compounds AVII) which are also new compounds of this invention. These dihydroxy compounds (Compounds AVII) may then be further treated to yield additional ketone final products of this invention (Compounds AVIII and AIX) which are also new final products of this invention. Thus, Compounds AVII may be treated with N-trimethylsilyldiethylamine at reduced temperature, followed by oxidation with a suitable oxidizing agent, for example, chromium trioxide-pyridine complex, and further followed by desilylation to yield the desired final ketone product of this invention (Compounds AVIII). These ketone final products (Compounds AVIII) may then be further treated as by dehydration, for example, by treatment with an acid catalyst, such as a mineral acid, among which are hydrochloric or sulfuric acids, to yield the unsaturated ketone final compounds (Compounds AIX) of this invention which are also new final products of this invention.

In the practice of this invention as aforesaid, the epoxy diol starting materials (Compounds XXIII and XXIV) are reacted with a fluorinated aluminum acetylide of the formula:

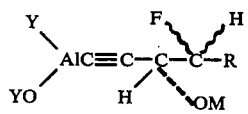

wherein each Y is alkyl; R is alkyl or alkenyl, or aralkyl; and M is hydrogen, alkyl or lower α-alkoxy alkyl. I have found that the most satisfactory results are obtained in the practice of this invention when the acetylide reactant employed is one which may be generally characterized as a fluorinated-alkyl-alkoxy-aluminum acetylide, and most preferably a fluorinated lower alkyl-lower alkoxy aluminum acetylide, for example, fluorinated methyl-methoxy aluminum acetylide.

Thus, relating back to the above structural formula, in the most preferred embodiment of this invention, each Y is lower alkyl, such as methyl; M is hydrogen or lower alkyl; F the fluoro substituent is in either the alpha- or beta-position; and R is lower alkyl or alkenyl. It should be understood that the substituents of Compounds III may be variously altered and/or modified and that these various substituents will be carried through to the final products of this invention. Thus, R may, in the preparation of Compounds AIII, be varied to include different lower alkyl moieties, such as propyl, butyl, pentyl or aralkyl moieties such as parafluorobenzyl, phenethyl, phenoxymethylene and the like, which will be carried through to the final product. The substituent M, in Compounds AIII, may also be varied in the preparation of Compounds AIII, and thus the respective variation, i.e. hydroxy or lower alkoxy or lower -alkoxyalkyl, will also carry through to the final products of this invention.

This invention thus also relates to the process for the production of the essential reagent, Compounds III, and these processes which entail a number of steps beginning with an alkyl alkanoate, such as ethyl-2-fluorohexanoate as starting material, may be represented by the following equations, wherein Y, R and M are as defined hereinafter:

$$\underset{O}{\overset{RO}{>}}C-CHF-R \longrightarrow \underset{HO}{\overset{HO}{>}}CHCHF-R \longrightarrow$$

AX       AXI
R = alkyl    R = alkyl $$HC\equiv C-\underset{H}{\overset{F}{C}}-\underset{OM}{\overset{H}{C}}-R \;+\; HC\equiv C-\underset{H}{\overset{F}{C}}-\underset{OM}{\overset{H}{C}}-R$$

AXII
a. M = H; R = alkyl
b. M = alkyl or lower α:alkoxyalkyl
   R = alkyl
c. M = OC₆H₄ (HOOC-); R = alkyl or aralkyl
d. M = OC₆H₄ (φ–CH(CH₃)–NH₃OOC-); R = alkyl or aralkyl AXIII
a. M = H; R = alkyl or lower alkoxyalky
b. M = alkyl; R = alkyl
c. M = OC₆H₄ (HOOC-); R = alkyl or aralky
d. M = OC₆H₄ (φ–CH(CH₃)–NH₃OOC-); R = alkyl or aralky $$\underset{YO}{\overset{Y}{>}}AlC\equiv C-\underset{H}{\overset{F}{C}}-\underset{OM}{\overset{H}{C}}-R$$

A III

Y = alkyl
M = H, or alkyl, or lower α-alkoxy alkyl
R = alkyl, or alkenyl, or aralkyl In the first step in the process for producing the desired halogenated aluminum acetylide, the alkylhaloalkanoate, starting material (Compounds AX), such as alkyl-fluoroalkanoate, for example, ethyl-2-fluorohexanoate is reduced as by treatment with a suitable reducing agent, for example, diisobutyl aluminum hydride to yield the respective halo alkanal hydrate (Compounds AXI). The haloalkanal hydrate (Compounds AXI) may then be processed to yield a mixture of the desired acetylenic compounds (Compounds AXII and AXIII), for example by treatment with an acetylenic magnesium halide, for example, acelylene magnesium bromide. The resultant mixture of these acelylenic compounds (Compounds AXII–AXIII) may be separated into their individual components by their conversion into the crystalline phthalate esters (Compounds AXIIc+AXIIIc) which can then be separated by fractional crystallization. These resultant phthalate esters may then be resolved into the optical antipodes by conversion into the salt with a suitable optically active amine, such as α-phenethylamine to yield the desired amine salt compounds (Compounds AXIId and AXIIId). The resultant amine salts are then hydrolyzed as by treatment with a base, such as an alkali metal base, for example sodium or potassium hydroxide to yield the free alcohols (Compounds AXIIa and AXIIIa). These free alcohols may then be converted into their respective alkyl ethers, for example, t-butyl-esters, by treatment with an alkylene and a mineral acid, such as isobutylene and hydrochloric acid to yield the desired alkyl ethers (Compounds AXIIb and AXIIIb). These alkyl ethers (Compounds AXIIb and AXIIIb) may then be transformed into their respective aluminum derivatives by reaction thereof with a lithium alkyl, such as butyllithium, followed by reaction with an alkyl akoxy aluminum halide, for example, methyl methoxy aluminum chloride to yield the desired halogenated aluminum acetylide reagents (Compounds AIII).

The instant invention may be illustrated by the following examples which are to be considered illustrative and not limitative of the instant invention:

EXAMPLE 1

Preparation of (±)-1,4-Dibenzyloxy-2-allyl-3-hydroxycyclopentane(II)

An etheral solution of allyl lithium (0.6 M, 0.25 mol) was added dropwise under nitrogen over a 15 min. period to a magnetically stirred suspension of purified CuI (19 g, 0.10 mol) in 250 ml of dry ether cooled to −78° with an acetone-dry ice bath. The dark brown allyl lithium cuprate complex was maintained at −78° for 5 min, and the epoxide (I) (14.8 g, 0.05 mol) in 250 ml of ether was then introduced dropwise at −78° over a 10 min period. The acetone-dry ice bath was immediately removed, the reaction mixture allowed to warm to room temperature and stirred for an additional 3 hours. After completion (the reaction was followed by GLC), the black reaction solution was quenched with 1.5 l. of saturated NH$_4$Cl solution and the solid copper salts removed by suction filtration through celite. The aqueous layer was extracted with ether (3×1500 ml), the ether layer washed with water (1×3000 ml), followed by drying over anhydrous Na$_2$SO$_4$. Evaporation of the ether under vacuum gave 17.22 g of a solid which was recrystallized from hexane to afford 15.3 g (90%) of the dibenzyl allyl alcohol (±)-II, mp 75°–76°

Anal. Calcd for C$_{22}$H$_{26}$O$_3$: C, 78.07; H, 7.74; Found: C, 78.12; H, 7.75.

EXAMPLE 2

Resolution of (±)-1,4-Dibenzyloxy-2-allyl-3-hydroxycyclopentane (a) Preparation of the α phenethyl urethane of 1,4-debenzyloxy-2-allyl-3-hydroxycyclopentane ((+)-XXX).

To a solution of 676 mg (2 mmoles) of the hydroxy compound (±)-II in 4 ml of dry toluene was added 330 mg (2.2 mmoles) of (+)-(R)-α-phenethyl isocyanate. The reaction mixture was refluxed for 24 hrs using a drying tube to exclude moisture. At the end of this period the solvent was removed on a rotary evaporator and finally in vacuo to furnish a crystalline residue. The latter was crystallized with ether and a small amount of hexane and recrystallized from ether-hexane. The pure material has mp 102.5°–103° $[\alpha]_D^{28}$+11.6° (c, 1.53 in CHCl$_3$).

(b) Preparation of (+)-1,4-dibenzyloxy-2-allyl-3-hydroxycylopentane

To a solution of 9.83 g of the urethane (+)-XXX in 300 ml of tetrahydrofuran was added 3.08 g of lithium aluminum hydride and the mixture refluxed for 1 hr under nitrogen. The reaction mixture was then cooled in ice-water and excess lithium aluminum hydride decomposed by dropwise addition of saturated sodium potassium tartrate through the reflux condenser. Upon completion of the decomposition the white precipitate was filtered through a sintered glass funnel and the residue on the filter washed with three 500 ml portions of ether. The combined filtrates were washed with 5% HCl (5×20 ml), with water until neutral and the ether layer dried over anhydrous sodium sulfate. Upon removal of the solvent in vacuo a soid (IIIa) is obtained which after recrystallization from hexane amounted to 6.662 g (91% yield). Mp 70°–71°$[\alpha]_D^{26}$+39° (c, 2.26 in CHCl$_3$).

EXAMPLE 3

Preparation of (−)-1,4-dibenzyloxy-2-allyl-3-hydroxycyclopentane (IVa)

Following the procedure of example 2 but substituting an equal amount of (−)-(S)-α-phenethyl isocyanate for the (+)-(R)-enantiomer there is obtained (−)-1,4-dibenzyloxy-2-allyl-3-hydroxycyclopentane.

EXAMPLE 4

(+)-1,4-Dibenzyloxy-2-allyl-3-tosyloxycyclopentane (IIIb)

A solution of 12.11 g of the (+)-compound of Example 2 and 8.8 g of p-toluenesulfonyl chloride in 18 ml of dry pyridine was allowed to stand at 25° for 24 hrs. An additional 2.2 g of tosyl chloride was then added and the mixture allowed to stand for an additional 24 hrs. At the end of this period the reaction mixture was cooled in an ice-water bath, 10 ml of water was added slowly and the mixture stirred for 10 min. It was then extracted with three 200 ml portions of ether and the combined ether layers washed with 2×100 ml of 5% hydrochloric acid, water, saturated sodium bicarbonate and again with water. The ether extract was dried over anhydrous sodium sulfate, the solvent removed and the light brown colored oil dried in high vacuum. The yield was 97.3%, $[\alpha]_D^{27}$+16.9° (c, 2.30 in CHCl$_3$).

The (+)-tosylate could not be crystallized. The racemate prepared by the same procedure melted at 57°–58°.

Anal: Calcd for $C_{29}H_{32}O_5S$: C, 70.71; H, 6.55; S, 6.50; Found: C, 70.37; H, 6.35; S, 6.72.

EXAMPLE 5

(−)-1,4-Dibenzyloxy-2-allyl-3-tosyloxycyclopentane (IVb)

Following the procedure of example 4 but substituting an equivalent amount of (−)-compound of Example 3 for the (+)-compound there is obtained (−)-1,4-dibenzyloxy-2-allyl-3-tosyloxycyclopentane $M_p$ 57°–58°; $[\alpha]_D^{28°} -17.8$ (c, 4.07 in $CHCl_3$).

EXAMPLE 6

Preparation of the Tosylate Acetal (IIIc)

A solution of 4.92 g of the (+)-allyl tosylate (IIIb) in 160 ml of methylene chloride was ozonized at −78°, the ozone being introduced at a rate of 300 ml/Min. The end point was determined by testing with postassium iodide. Upon completion the reaction mixture was immediately poured into vigorously stirred zinc dust (10 g) and 16 ml of acetic acid. After two hrs stirring the KI test was negative and the mixture was filtered through celite and the filter cake washed thoroughly with methylene chloride. The filtrate was washed with 5% HCl, sodium bicarbonate and water and dried over anhydrous magnesium sulfate. The solvent was then removed in vacuo and the crude product acetalized by addition of 20 ml of ethylene glycol, 10 ml of benzene and 0.2 ml of $BF_3$-etherate. After vigorous stirring for 24 hrs under nitrogen at 25° five ml of water was added and the mixture extracted with three 150 ml portions of ether. The combined ether extracts were washed with saturated bicarbonate, water and saturated sodium chloride solution and dried over sodium sulfate. Removal of the solvent left a light yellow oil, which could not be induced to crystallization. $[\alpha]_D^{26°} +5.4°$ (c, 4.48 in $CHCl_3$). The racemic acetal tosylate had mp 74°–75° after crystallization from ether hexane.

Anal. Calcd for $C_{30}H_{34}O_7S$ C, 66.90; H, 6.36; S, 5.94; Found: C, 66.72; H, 6.35; S, 6.18.

EXAMPLE 7

Preparation of the (−)-Tosylate Acetal (IVc)

Following the procedure of example 6 but substituting an equivalent amount of the (−)-allyl tosylate for the (+)-allyl tosylate was obtained the (−)-tosylate acetal $[\alpha]_D^{27°} -4.6°$ (c, 3.14 in $CHCl_3$).

EXAMPLE 8

Preparation of the Dibenzyloxyhydroxy tosylate [(+)-XXVa]

A solution of 10 g of the (+)-dibenzyl allyl tosylate in 280 ml of methylene chloride was ozonized at −78° at a flow rate of 400–500 ml/min of gas. After 40 min completion of the ozonolysis was indicated by the appearance of a pale blue color in the reaction vessel and by a positive KI test. The solution was immediately transfered to a round bottom flask containing 1.8 g of sodium borohydride in 120 ml of isopropyl alcohol was added and the reaction mixture stirred a room temperature for 20 hrs. The mixture was then poured into ice water, acidified with 6 N HCl to pH 2 and extracted with three 500 ml portions of chloroform. The chloroform extracts were washed successively with 5% sodium bicarbonate, water, saturated sodium chloride solution, and dried over anhydrous sodium sulfate. Removal of the solvents in vacuo gave 9.73 g (96%) of the (+)-dibenzyl tosylate alcohol as a viscous oil. An analytical sample was prepared by tlc. $[\alpha]_D^{27°} +3.7°$ (c, 2.14 in $CHCl_3$).

Anal. Calcd for $C_{28}H_{32}O_6S$ C, 67.72; H, 6.49; S, 6.46; Found: C, 67.92, H, 6.59; S, 6.57.

EXAMPLE 9

Preparation of (−)-Dibenzyl allyl tosylate alcohol (Antipode of XXVa)

Following the procedure of Example 8 but substituting an equivalent amount of (−)-dibenzyl allyl tosylate for the (+)-dextrorotatory antipode of Example 4 there was obtained the (−)-dibenzyl allyl tosylate alcohol.

EXAMPLE 10

Preparation of the (+)-Diol acetal tosylate (IIId)

A solution of 2.69 g of the (+)-dibenzyl ether tosylate of Example 6 and 1.0 g of potassium acetate in 200 ml of 95% ethanol and 10 ml of glacial acetic acid was stirred in an atmosphere of hydrogen in the presence of 2.4 g of 10% palladium on charcoal. After stirring for 24 hrs. 3 g of fresh catalyst was added and the reaction allowed to proceed for another 24 hrs. The reaction mixture was then filtered through celite and the filtrate was neutralized by dropwise addition of potassium carbonate in methanol with ice cooling until the solution was neutral. The solvents were then removed in vacuo keeping the bath temperature below 40°. Ether and ethyl acetate was then added and the mixture washed once with saturated bicarbonate, sodium chloride and dried over anhydrous magnesium sulfate. The solvent was removed and the crude (+)-diol purified by chromatography on silica gel. $[\alpha]_D^{26°} +9.9°$ (c, 0.96 in $CHCl_3$).

Anal. Calcd for $C_{16}H_{22}O_7S$ C, 53.63; H, 6.19; S, 8.93; Found: C, 53.56; H, 6.23; S, 8.95.

EXAMPLE 11

Preparation of (−)-Diol acetal tosylate (IVd)

Following the procedure of Example 10 but substituting an equivalent amount of the (−)-dibenzyl ether of Example 7 there was obtained the (−)-diol. $[\alpha]_D^{27°} -14.7°$ (c, 2.89 in $CHCl_3$).

EXAMPLE 12

Preparation of the (+)-Triol tosylate (XXVb)

A solution of 5.1 g of the (+)-dibenzyl tosylate alcohol of Example 8 in 190 ml of ethyl acetate saturated with water was stirred with 3.5 g of 10% palladium on charcoal in an hydrogen atmosphere. After the theoretical amount of hydrogen was consumed, which required approximately 1 hr, the reaction mixture was filtered through a sintered glass funnel containing celite and the catalyst thoroughly washed with 500 ml of ethyl acetate. The ethyl acetate was removed under vacuum affording 3.4 g (87% yield) of the (+)-triol tosylate as a viscous oil. $[\alpha]_D^{26°} +27.0°$ (c, 1.98 in $CHCl_3$).

EXAMPLE 13

Preparation of the (−)-Triol Tosylate (Antipode of XXVb)

Following the procedure of Example 12 but substituting an equivalent amount of the (−)-dibenzyl tosylate alcohol of Example 9 for the dextrorotatory enantiomer there was obtained the (−)-triol tosylate.

EXAMPLE 14

Preparation of the (−)-Epoxy acetal (V)

A solution of the (+)-diol tosylate of Example 10 in 16 ml of 2% methanolic KOH, was stirred at 25° for 2 hrs. The methanol was removed in vacuo at a bath temperature below 35° and 10 ml of water was added. The resulting mixture was extracted three times with ether/ethyl acetate, the organic layer washed once with saturated sodium chloride containing bicarbonate and dried over anhydrous magnesium sulfate. After removal of the solvents in vacuo the crude (−)-epoxy acetal was purified by chromatography on silica gel. $[\alpha]_D^{25°} -6.9°$ (c, 2.4 in $CHCl_3$).

Anal. Calcd for $C_9H_{14}O_4$ C, 58.05; H, 7.58; Found: C, 57.72; H, 7.39.

EXAMPLE 15

Preparation of the (+)-Epoxy acetal (XI)

Following the procedure of Example 14, but substituting an equivalent amount of the (−)-diol tosylate of Example 11 for the destrorotatory enantiomer there was obtained the (+)-epoxy acetal. $[\alpha]_D^{26°} +7.4°$ (c, 3.58 in $CHCl_3$).

EXAMPLE 16

Preparation of the (+)-Epoxy diol (XXIIIa)

Following the procedure of Example 14, but substituting an equivalent amount of the (+)-triol tosylate of Example 12 for the (+)-diol tosylate acetal there was obtained the (−)-diol epoxide. $[\alpha]_D^{26°} +1.8°$ (c, 2.0 in $CHCl_3$).

EXAMPLE 17

Preparation of (−)-Epoxy diol (XXIVa)

Following the procedure of Example 14, but substituting an equivalent amount of the (−)-triol tosylate of Example 13 for the (+)-diol tosylate acetal there was obtained the (−)-diol epoxide. $[\alpha]_D^{26°} -1.4°$ (c, 1.67 in $CHCl_3$).

EXAMPLE 18

Alternate route for the preparation of the (+)- and (−)-Diol Epoxides (XXIIIa and XXIVa)

(a) Preparation of (∓)-cis-2-(2′-hydroxyethyl-)cyclopent-3-ene-ol (XXIIa).

A solution of the cyclopentene lactone (±)-XXI in 50 ml of tetrahydrofuran was added with stirring over 15 min at 0° to a suspension of 1.74 g of lithium aluminum hydride in 100 ml of tetrahydrofuran. The mixture was stirred for an additional 45 min at 0° whereupon saturated aqueous potassium sodium tartrate was added dropwise until no further hydrogen was evolved. Excess anhydrous sodium sulfate was added, the mixture was filtered and the filter thoroughly washed with tetrahydrofuran. The solvent was evaporated at 30° to give a viscous pale yellow liquid which was distilled to give 3.5 g of the diol olefin (±)-XXIIa $Bp_{1.6mm}$ 108° (90% yield).

EXAMPLE 19

Resolution of the Cyclopentenediol (±)-XXIIa (a) Preparation of the (−)-Bis-(R)-N-(α-phenethyl-)carbamate of the Dihydroxy pentenediol A solution of 1.855 g of the (±)-racemic cyclopentene-diol XXIIa in 30 ml of dry toluene was added under nitrogen to a solution of 4.874 g of freshly distilled (+)-(R)α-phenethylisocyanate in 70 ml of dry toluene and the mixture was refluxed for 17 hrs, whereupon the reaction was judged to be complete by tlc on silica gel. The hot solution was filtered, the solvent evaporated and the yellow solid dissolved in 20 ml of benzene. Crystallization from the cold solution was spontaneous. Yielding 2.937 g of solid mp 135°–142°. Recrystallization from 12 ml of hot benzene afforded 2.329 g of material, mp 143.6°–145°. A second crystallization from 10 ml of hot benzene afforded 2 g of pure (−)-XXXI. Mp 147.0°–148° (65% yield). $[\alpha]_D^{50°} -57.3°$ (c, 1.0 in benzene).

Anal. Calcd for $C_{25}H_{30}O_4N_2$ C, 71.06; H, 7.16; N, 6.63; Found: C, 70.96; H, 7.00; N, 6.62.

(b) Preparation of (−)-cis-2-(2′-hydroxyethyl-)cyclopent-3-ene-ol (XXIIc)

A solution of 2.2 g of the (−)-biscarbamate (XXXI) in 25 ml of tetrahydrofuran was added at reflux to a suspension of 540 mg of lithium aluminum hydride in 75 ml of tetrahydrofuran and the mixture was stirred and refluxed for 2 hrs. It was then cooled and saturated aqueous potassium sodium tartrate was added dropwise until no further hydrogen was evolved. Excess anhydrous sodium sulfate was added, the suspension was filtered and the filter thoroughly rinsed with tetrahydrofuran. The solvent was evaporated in vacuo and the residue taken up in 20 ml of methanol. The resulting solution was passed through a column containing 10 g (2.5 equiv) of 50–100 mesh Dowex 50W-X8 previously washed with 0.1 N hydrochloric acid, distilled water and methanol and the column was rinsed with 20 ml of methanol. Evaporation of the solvent at 30° afforded 408 mg of a yellow oil which upon distillation afforded 408 mg of pure (−)-cyclopentenediol $[\alpha]_D^{25°} -54.6°$ (c, 1.06 in $CHCl_3$).

EXAMPLE 20

Preparation of (+)-cis-2-(2′-hydroxyethyl-)cyclopent-3-ene-ol

Following the procedure of Example 19 but substituting an equivalent amount of (−)-(S)-1-phenethyl isocyanate for the (+)-(R)-enantiomer there was obtained (+)-XXIIb. $[\alpha]_D^{26°} +57.7°$ (c, 1.08 in $CHCl_3$).

EXAMPLE 21

Preparation of the (+)-Epoxy diol (XXIIIa)

A solution of 2.4 g of 85% m-chloroperbenzoic acid in 30 ml chloroform was added at 0° to a solution of 1.2 g of the (−)-ent-diol (XXIIc) in 20 ml of chloroform and the mixture was stirred at 0° for 3 hrs. Methanol was added to the resultin white suspension and the mixture was partially evaporated at room temperature. This was repeated twice and methanol was added to make up to 100 ml. This solution was passed through a short column containing 17.7 g (2.5 equiv) of 100–200 mesh Dowex 1-X8 previously washed with 300 ml of 0.5 N sodium hydroxide distilled water and 300 ml of methanol and the column was rinsed with 150 ml of methanol. Evaporation of the solvent at 30° afforded a yellow oil which was distilled to give 1.435 of pure (+)-epoxy diol as a viscous colorless liquid. Bp 60° bp$_{0.14 \, mm \, Hg}$ 60° (99.6% yield). $[\alpha]_D^{25°}$ +2.7° (c, 2.36 in CHCl$_3$).

Anal. Calcd for C$_7$H$_{12}$O$_3$ C, 58.31; H, 8.39; Found: C, 58.33; H, 8.51.

EXAMPLE 22

Preparation of the (−)-Epoxy diol (XXIVa)

Following the procedure of Example 21 but substituting an equivalent amount of the (+)-cyclopentene diol of Example 20 for its levorotatory antipode there was obtained the enantiomeric(−)-epoxy diol (XXIVa).

EXAMPLE 23

Preparation of (−)-Methoxymethyl-t-butoxyoctynyl alane (VIIa)

(a) Preparation of methoxymethyl aluminum chloride

Thirty ml of a solution of 1.4 M dimethylaluminum chloride in toluene (42 mmoles) was placed in a 100 ml three-neck flask equipped with a magnetic stirrer, a nitrogen inlet adapter, a rubber septum and a dropping funnel. The reaction flask was then cooled to 0.5° in an ice bath and dry methanol (40 mmoles) in 8 ml of dry toluene was added dropwise over a 5 min period to the magnetically stirred solution of dimethylaluminum chloride. Upon completion of the reaction the ice bath was removed and the solution allowed to stir at 25° for a additional 20 min. The resulting solution of methoxymethyl methyl aluminum chloride was transferred under nitrogen to a clean dried amber bottle fitted with a septum and stored under nitrogen.

(b) Preparation of (−)-(S)-Monomethoxymethyl t-butoxyoctynyl alane

In a 2-neck round bottom flask equipped with a magnetic stirrer, condenser, nitrogen inlet and rubber septum was placed a solution of 13 equiv of (−)-(S)-3-t-butoxyoctynol in 4 ml of dry toluene and the contents cooled to 0°-5° in an ice-water bath. Addition of n-butyl lithium in hexane (13 equiv) at 0°-5° over a 15 min period was followed by addition of methoxymethyl aluminum chloride (9 equiv) at 0°-5° over a 50 min period which produced a colorless to pale yellow solution. The ice-water bath was removed and the (−)-alane reagent was allowed to remain at room temperature for 5 min before addition of epoxide to be described in subsequent examples.

EXAMPLE 24

Preparation of the Alane Reagent (VIIb)

Following the procedure of Example 23 but substituting an equivalent amount of (−)-(S)-3-t-butoxy-cis-octene-3-ol-1-yne for (−)-(S)-t-butoxy-1-octyne there was obtained the corresponding alane reagent (VIIb).

EXAMPLE 25

Preparation of the Alane Reagent (VIIc)

Following the procedure of Example 23 but substituting an equivalent amount of (−)-(S)-3-trimethyl-silyloxy-cis-oct-5-ene-1-yne for (−)-(S)-3-t-butoxy-1-octyne there was obtained the corresponding silylated alane reagent (VIIc).

EXAMPLE 26

Preparation of the (−)-(S)-t-Butoxyoctylnylcyclopentanediolacetal (VIIIa).

To the solution of the (−)-methylmethoxyoctynyl alane reagent precisely as prepared in Example 23, is added a solution of 186 mg (1 mmole) of the (−)-hydroxy acetal epoxide of Example 14 in 2 ml of toluene and the mixture stirred at 80° for 4–6 hrs. The reaction was followed by checking for disappearance of starting material in an aliquot by glc. When the unreacted epoxide peak was less than 5% of the product peak the reaction mixture was cooled to 0°-5° and saturated sodium sulfate was added dropwise. A solid cement-like precipitate was formed and after stirring vigorously for 10 min., 200 ml of ether was added, the layers were separated and the ether solution dried over anhydrous sodium sulfate. The solution was concentrated under ordinary pressure to remove the ether, and the toluene and residual t-butoxyoctyne distilled off and collected in a dry ice trap. The trapped material was then purified by fractional distillation for reuse. The residual product was dried in vacuo and chromatographed on 30 g of silica gel with benzene-ethyl acetate. Mixtures of 10:1 and 5:1 benzene-ethyl acetate removed impurities which were followed by the position isomer of (−)-VIIIa with 2:1 benzene-ethyl acetate and finally by (−)-VIIIa itself (174 mg) with the same solvent mixture $[\alpha]_D^{26°}$ −35.8° (c, 1.90 in CHCl$_3$).

EXAMPLE 27

Preparation of (−)-(S)-t-Butoxyoctynylcyclopentanediol acetal (IXa)

Following the procedure of Example 26, but substituting an equivalent amount of the (+)-epoxy acetal of Example 15 for the (−)-epoxide, there was obtained the desired (−)-acetal (IXa) $[\alpha]_D^{25°}$ −42° (c, 2.00 in CHCl$_3$).

EXAMPLE 28

Preparation of (−)-(S)-t-Butoxyoctynylcyclopentanetriol (XXVIa)

Following the procedure of Example 26 but substituting the (+)-epoxy diol of Example 16 for the (−)-epoxide (V), there was obtained the (−)-pentanetriol (XXVIa) $[\alpha]_D^{26}$ −35.0° (c, 3.22 in CHCl$_3$).

Anal.: Calcd for C$_{19}$H$_{34}$O$_4$: C, 69.91; H, 10.50. Found: C, 69.98; H, 10.59.

EXAMPLE 29

Preparation of diastereomer of (−)-(S)-Butoxyoctynylcyclopentanetriol (XXVIIa)

Following the procedure of Example 26 but substituting an equivalent amount of the (−)-diol epoxide of Example 17 for the (+)-dextrorotatory enantiomer, there was obtained the diastereomeric butoxyoctynyl triol (XXVIIa). $[\alpha]_D^{28}$ −46.8° (c, 1.7 in CHCl$_3$).

EXAMPLE 30

Preparation of t-Butoxyoctenynylcyclopentanediol acetal (VIIIb)

Following the procedure set forth in Example 26 but substituting an equivalent amount of the t-butoxyoctenynyl alane of Example 24 for the (−)-t-butoxyalkynyl alane, there was obtained the t-butoxyoctenynylcyclopentanediol acetal (VIIIb).

EXAMPLE 31

Preparation of t-Butoxyoctenynylcyclopentanediol acetal (IXb)

Following the procedure of Example 26 but substituting the (S)-t-butoxyoctenynyl methyl methoxy alane of Example 24 for the (−)-alane, there was obtained the t-butoxyoctenynylcyclopentanediol acetal.

EXAMPLE 32

Preparation of the (−)-t-Butoxy hemiacetal (Xa)

A solution of 51.4 mg of the (−)-ethylene acetal of Example 26 in 4 ml of 0.1 N HCl acetonitrile:water (2:1) was stirred at 25° for 48 hrs. 100 ml of chloroform was then added to the reaction mixture and the resulting mixture washed with brine and dried over anhydrous sodium sulfate. Removal of the solvents in vacuo gave the crude (−)-hemiacetal which was purified by silica gel tlc, (yield 90%) $[\alpha]_D^{25} -45.2°$ (c, 1.83 in CHCl$_3$).

EXAMPLE 33

Preparation of the (−)-t-Butoxy hemiacetal (XIa)

Following the procedure of Example 32, but substituting an equivalent amount of the (−)-acetal of Example 27 for the (−)-diastereomeric acetal there was obtained the (−)-t-butoxy hemiacetal $[\alpha]_D^{27} -39.3°$ (c, 1.76 in CHCl$_3$).

EXAMPLE 34

Preparation of t-Butoxyoctenynyl hemiacetal (Xb)

Following the procedure of Example 32 but substituting an equivalent amount of the acetal of Example 30 for the (−)-acetal there was obtained the corresponding hemiacetal.

EXAMPLE 35

Preparation of the t-Butoxyoctenynyl hemiacetal (XIb)

Following the procedure of Example 32 but substituting an equivalent amount of the acetal of Example 31 for the (−)-acetal there was obtained the hemiacetal.

EXAMPLE 36

Preparation of t-Butoxyoctenynylcyclopentanetriol (XXVIb)

Following the procedure of Example 26 but substituting an equivalent amount of the (+)-epoxy diol of Example 21 for the (−)-epoxide and an equivalent amount of the t-butoxyoctenynyl alane of Example 24 for the (−)-t-butoxyoctynyl alane there was obtained the corresponding t-butoxyoctenynylcyclopentanetriol.

EXAMPLE 37

Preparation of the t-Butoxyoctenynylcyclopentanetriol (XXVIIb)

Following the procedure of Example 26 but substituting an equivalent amount of the (−)-epoxy diol of Example 22 for the (−)-epoxide and an equivalent amount of the t-butoxyoctenynyl alane of Example 24 for the (−)-t-butoxyoctynyl alane there was obtained the t-butoxyoctenynylcyclopentanetriol.

EXAMPLE 38

Preparation of the (−)-t-Butoxy Lactone (XXVIIIa)

Platinum dioxide (150 mg, Engelhart lot no 46) was reduced with hydrogen at room temperature under atmospheric pressure in 22 ml of distilled water for 12 min. The reaction vessel was then successively evacuated and filled with nitrogen (4 times) and air (4 times), after which time oxygen was bubbled into the catalyst mixture for 5 min. 150 Mg of the (−)-octnynyl triol of Example 28 in 14 ml of water:acetone (4:1) was added over a period of 2 min via an addition funnel. The funnel was washed with 2 ml of water:acetone (4:1) and 1.6 ml of acetone. The reaction flask was then placed in an oil bath at 57° and oxygen introduced directly into the heterogeneous mixture. The progress of the reaction was followed by glc. After completion (3–4 hrs) the catalyst was filtered by suction through celite and the celite thoroughly washed with ethyl acetate. The aqueous layer was extracted 3 times with ethyl acetate and the combined ethyl acetate extracts successively washed witH 5% HCl and saturated sodium chloride solution and then filtered with suction through a pad of anhydrous sodium sulfate. Removal of the solvent in vacuo gave the crude lactone which was purified by column chromatography on silica gel to afford the pure (−)-lactone in 85% yield. $[\alpha]_D^{26°} -39.6°$ (c, 3.61 in CHCl$_3$).

Anal. Calcd for $C_{19}H_{30}O_4$ C, 70.77; H, 9.38; Found: C, 70.49; H, 9.54.

EXAMPLE 39

Preparation of the Diastereomeric Lactone (XXIXa)

Following the procedure of Example 36 but substituting an equivalent amount of the diastereomeric triol in Example 29 for the (−)-triol there was obtained the diastereomeric lactone $[\alpha]_D^{28°} -49.3°$ (c, 1.5 in CHCl$_3$).

EXAMPLE 40

Preparation of the t-Butoxyenyne Lactone (XXVIIIb)

Following the procedure of Example 38 but substituting an equivalent amount of the t-butoxyenyne triol of Example 36 for the (−)-triol (XXVIa), there was obtained the corresponding lactone.

EXAMPLE 41

Preparation of the Diastereomeric t-Butoxyenyne Lactone (XXIXa)

Following the procedure of Example 38 but substituting an equivalent amount of the diastereomeric t-butoxyenyne triol of Example 37, for the (−)-octynyl triol (XXVIIa) there was obtained the diastereomeric t-butoxyenynyl lactone.

EXAMPLE 42

Alternate Preparation of the (−)-Hemiacetal (Xa)

To a solution of 87 mg of the (−)-t-butoxyoctynyl lactone of Example 38 in 1.5 ml of toluene was added at −65° 0.62 mmol of a 1.2 M solution of diisobutylaluminum hydride in toluene. The reaction was complete after 1 hr upon which the mixture was acidified with 5% hydrochloric acid and the reaction mixture was allowed to warm to room temperature. Solid anhydrous sodium sulfate in ethyl acetate was added, the mixture stirred vigorously and the solid salts removed by suction filtration. Removal of the solvent in vacuo gave the crude (−)-hemiacetal $[\alpha]_D^{26°} -49.5°$ (c, 2.43 in $CHCl_3$).

EXAMPLE 43

Alternate Preparation of Diastereomeric Hemiacetal [(−)-XIa]

Following the procedure of Example 42 but substituting an equivalent amount of the (−)-diastereomeric lactone of Example 39 for the (−)-lactone (XXVIIIa) there was obtained the diastereomeric hemiacetal.

EXAMPLE 44

Alternate Preparation of the Hemiacetal (Xb)

Following the procedure of Example 42 but substituting an equivalent amount of the t-butoxyoctenynyl lactone of Example 40 for the (−)-lactone there was obtained the hemiacetal.

EXAMPLE 45

Alternate Preparation of the Hemiacetal (XIb)

Following the procedure of Example 42 but substituting an equivalent amount of the diastereomeric t-butoxyoctenynyl lactone of Example 41 for the (−)-lactone (−)-XXVIIIa there was obtained the hemiacetal (XIb).

EXAMPLE 46

Preparation of (+)-13-Dehydro-$PGF_{2\alpha}$ (XIIa)

Into a 2-neck round bottom flask dried and flushed with nitrogen was placed 1.1 mmol NaH (53%, 11 equiv., 50 mg), which had been washed three times with dry hexane under nitrogen, followed by addition of 0.5 ml of dry dimethylsulfoxide (freshly distilled over CaH and stored over molecular sieves). The resulting suspension was heated at a bath temperature of 70°–75° for 1 hr, the resulting grayish-green solution cooled to 25°, and 0.6 mmol (268 mg) of 5-triphenylphosphoniovaleric acid bromide (dried under vacuum at 70° C. for 24 hrs.) dissolved in 0.4 ml of DMSO added slowly by syringe through a rubber septum. To the resulting red solution was added after 10 min a solution of 0.1 mmole (27.0 mg) the (−)-hemiacetal of Example 42 in 0.1 ml of DMSO, and the mixture heated with stirring at 50° for 4 hrs. The reaction was followed by glc analysis. For this purpose aliquots were taken, acidified with 1 drop of aqueous HCl followed by extraction with ethyl acetate, drying with magnesium sulfate and removing the solvent until the hemiacetal glc peaks had disappeared. When the reaction was complete (4–6 hrs) the mixture was transfered into an Erlenmeyer flask, cooled to 0°–5° and acidified with 5% HCl in saturated NaCl, followed by extration with ethyl acetate. The combined ethyl acetate layers were washed once more with brine and dried over sodium sulfate. Removal of the solvent in vacuo at 50° for 1 hr gave the crude product. This material was dissolved in a 1:2 mixture of ethyl acetate-ether seeded with triphenylphosphonio valeric acid and allowed to remain in the freezer overnight. Crystals of the unreacted acid formed, which were removed by filtration. The ethyl acetate-ether solution was concentrated in vacuo, dried in vacuo overnight and 0.5 ml of trifluoroacetic acid was added and the mixture stirred at 0°–5° for four hrs. Methanol-water was then added and the mixture evaporated to dryness on the rotary evaporator at a bath temperature of 35°. To remove small amounts of trifluoroacetyl esters 1 ml of 2% methanolic KOH was added and the mixture stirred for 30 min. After removal of the methanol the residual mixture was diluted with water and extracted exhaustively with ether to remove triphenylphosphine oxide and residual starting material. The aqueous solution was acidified with hydrochloric acid saturated with sodium chloride and extracted four times with ethyl acetate. The combined ethyl acetate extracts were washed with brine, dried over sodium sulfate and the solvent removed in vacuo. The residue was silylated with trimethylchlorosilane and hexamethyl disilazene in pyridine for 1–2 hrs at 25°. Upon addition of hexane a precipitate formed which was removed by centrifugation. Upon cooling additional amounts of crystalline material precipitated, crystallization being complete after standing in the refrigerator overnight. The hexane solution was evaporated and dried in vacuo and the material checked by glc. If additional amounts of triphenylphosphine oxide and the triphenylphosphonio valeric acid remained, crystallization from hexane was repeated. The hexane solution was evaporated to dryness and stirred with methanol-water-acetic acid (10:1:1) at 25° for 1 hr followed by removal of the solvents in vacuo. The residue consisted of crude 13-dehydro $PGF_2$ which was purified by high pressure chromatography of silica gel. The pure material has $[\alpha]_D^{26°} +33.7°$ (c, 1.39 in ethanol), mp 50°–52°.

EXAMPLE 47

Preparation of the (−)-Enantiomer of 15-epi-13-Dehydro-$PGF_{2\alpha}$

Following the procedure described in Example 46 but substituting an equivalent amount of the (−)-hemiacetal of Example 43 for the (−)-hemiacetal (Xa) there was obtained the enantiomer of 15-epi-13-dehydro-$PGF_{2\alpha}$. Mp 22°–23°; $[\alpha]_D^{27°} -39.3°$ (c, 0.93 in ethanol). Anal. Calcd. for $C_{20}H_{32}O_5$ C, 68.15; H, 9.15. Found: C, 67.61; H, 8.89.

EXAMPLE 48

Preparation of 13-Dehydro-$PGF_{3\alpha}$ (XIIc)

Following the procedure of Example 46, but substituting the hemiacetal of Example 44 for the (−)-hemiacetal (Xa) there was obtained 13-dehydro-$PGF_{3\alpha}[\alpha]_D^{25°} +38°$ (c, 0.22 in ethanol).

EXAMPLE 49

Preparation of the Enantiomer of 15-epi-13-Dehydro-$PGF_{3\alpha}$ (XIIIc)

Following the procedure of Example 46 but substituting the hemiacetal of Example 45 for the (−)-hemiacetal (Xa) there was obtained the enantiomer of 15-epi-13-dehydro-$PGF_{3\alpha}$ (XIIIc).

EXAMPLE 50

Preparation of the (−)-13-cis-Isomer of $PGF_{2\alpha}$ (XIIe)

In a small glass vial equipped with a clean teflon magnetic stirring bar and a rubber septum cap, 8.5 mg 5% Pd on $BaSO_4$ (Engelhard no. 13,417) was prehydrogenated for 15 min at atmospheric pressure in 0.5 ml of dry pyridine. A solution of 10.9 mg of 13-dehydro-$PGF_{2\alpha}$ $[\alpha]_D^{26.5°} +35.0°$; (c, 2.02 in EtOH) in 40 μl of dry pyridine was injected into the black suspension of catalyst and washed with four 10 portions of pyridine. The mixture was stirred at room temperature under one atmosphere of hydrogen for 1.0 hour. After 45 min the black suspension had turned gray and to some black granules. The mixture was diluted with diethyl ether and centrifuged. The supernatant was concentrated by blowing off volatiles with a stream of nitrogen. More ether was added and blown off to help remove residual pyridine. The crude material was dried in vacuo at room temperature for 16 hours to give 10.0 mg of a slightly colored very viscous oil. Tlc on cilica gel using benzene-dioxane-acetic acid 20:20;1 development showed no starting material, an intense spot due to (−)-13-cis-isomer of $PGF_{2\alpha}$ significantly less polar than the starting material, a very faint spot having exactly the same $R_f$ value as $PGF_{2\alpha}$ (13-trans) and a very faint spot just above this.

The crude was purified by high pressure column chromatography on a 48×0.3 cm column of silica gel (0.9 g). Twenty-five 100 drop fractions were collected while eluting with 4:1 benzene ethyl acetate and one hundred 100 drop fractions were collected while eluting with 3:2 benzene-ethyl acetate. Based on analysis of fractions by tlc fractions 36–75 were combined and concentrated in vacuo to give 7.4 mg of pure (−)-13-cis-$PGF_2$ as a nearly colorless oil. Yield=68% of theory. Tlc on silica gel using benzene-dioxane-acetic acid 20:20:1 development showed only one spot. Tlc on silica gel impregnated with silver nitrate using the same developer showed one very intense spot and two very faint spots of much higher $R_f$ value. $[\alpha]_D^{25°} -24.6°$ (c, 0.70 in ethanol).

EXAMPLE 51

Preparation of the (+)-Enantiomer of 13-cis-15-epi-$PGF_{2\alpha}$ (XIIIe)

Following the procedure of Example 50 but substituting an equivalent amount of the (−)-diastereomeric enantiomer of 15-epi-13-dehydro-$PGF_{2\alpha}$ of Example 47 for (+)-13-dehydro-$PGF_{2\alpha}$ there was obtained the enantiomer of 13-cis-15-epi-$PGF_{2\alpha}$.

EXAMPLE 52

Preparation of 13-cis-$PGF_{3\alpha}$ (XIIg)

Following the procedure of Example 50, but substituting an equivalent amount of 13-dehydro-$PGF_{3\alpha}$ of Example 48 for 13-dehydro-$PGF_{2\alpha}$ there was obtained 13-cis-$PGF_{3\alpha}$.

EXAMPLE 53

Preparation of the Enantiomer of 13-cis-15-epi-$PGF_{3\alpha}$ (XIIIg)

Following the procedure of Example 50, but substituting an equivalent amount of the enantiomer of 13-dehydro-15-epi-$PGF_{3\alpha}$ of Example 49 for 13-dehydro-$PGF_{2\alpha}$ there was obtained the enantiomer of 13-cis-15-epi-$PGF_{3\alpha}$.

EXAMPLE 54

Preparation of 13-Dehydro-$PGE_2$ Methyl ester (XIVb)

To a solution of 20 mg of $PGF_{2\alpha}$ methyl ester (prepared from $PGF_{2\alpha}$ and ethereal diazomethane for 10 min at 0° followed by evaporation of the solvent) in 0.4 ml of dry acetone was added with stirring at −40° under nitrogen 0.8 ml of N-trimethylsilyldiethylamine. After 1 hr the reaction was quenched with 0.6 ml of dry methanol and the mixture allowed to warm to 25°. Evaporation to dryness under reduced pressure yielded as the major product the 11,15-bis-trimethylsilyl derivative of (+)-13-dehydro-$PGF_{2\alpha}$, which was oxidized with Collins reagent in situ (prepared from 36 mg of $CrO_3$ and 55 μl of pyridine in 0.8 ml of $CH_2Cl_2$) for 5 min at 25° followed by desilylation with a mixture of 1 ml of methanol, 0.1 ml of water and 0.05 ml of acetic acid for 1 hr. High pressure chromatography on silica gel afforded on elution with varying ratios of hexane-ethyl acetate 10 mg of 13-dehydro-$PGE_2$ methyl ester in 41% yield from (+)13-dehydro-$PGF_{2\alpha}$. Mass spectrum of the bis-trimethylsilyl ether: $M^+ 508$.

EXAMPLE 55

Preparation of the Enantiomer of 13-Dehydro-15-epi-$PGE_2$ (XVb) Methyl Ester

Following the procedure of Example 54 but substituting an equivalent amount of the (−)-enantiomer of 13-dehydro-15-epi-$PGF_{2\alpha}$ methyl ester for the 13-dehydro-$PGF_{2\alpha}$ methyl ester there was obtained the (−)-enantiomer of 13-dehydro 15-epi-$PGE_3$ methyl ester. $[\alpha]_D^{28°} -5.6°$ (c, 0.45 in ethanol). Mass spectrum of the bis-trimethylsilyl ether: $M^+ 508$.

EXAMPLE 56

Preparation of 13-Dehydro-$PGE_3$ Methyl ester (XIVd)

Following the procedure of Example 54 but substituting an equivalent amount of 13-dehydro-$PGF_{3\alpha}$ methyl ester for the 13-dehydro-$PGF_{2\alpha}$ methyl ester there was obtained the 13-dehydro-$PGE_3$ methyl ester.

EXAMPLE 57

Preparation of the Enantiomer of 13-Dehydro-15-epi-$PGE_3$ (XVd) Methyl ester

Following the procedure of Example 54 but substituting an equivalent amount of the anantiomer of 13-dehydro-15-epi-$PGF_{3\alpha}$ methyl ester for the 13-dehydro-$PGF_{2\alpha}$ methyl ester there was obtained the enantiomer of 13-dehydro-15-epi-$PGE_3$ methyl ester.

EXAMPLE 58

Preparation of 13-cis-$PGE_2$ Methyl ester (XIVf)

Following the procedure of Example 54 but substituting an equivalent amount of (−)-13-cis-$PGF_{2\alpha}$ methyl ester for the 13-dehydro-$PGF_{2\alpha}$ methyl ester there was obtained 13-cis-$PGE_2$ methyl ester.

EXAMPLE 59

Preparation of the Enantiomer of 13-cis-$PGE_2$ Methyl ester

Following the procedure of Example 54 but substituting an equivalent amount of the enantiomer of 13-cis-15-epi-$PGF_{2\alpha}$ methyl ester for 13-dehydro-$PGF_{2\alpha}$ methyl ester there was obtained the enantiomer of 13-cis-15epi-$PGE_2$.

EXAMPLE 60

Preparation of 13-cis-$PGE_3$ Methyl ester (XIVh)

Following the procedure of Example 54 but substituting an equivalent amount of 13-cis-$PGF_{3\alpha}$ methyl ester for the 13-dehydro-$PGF_{2\alpha}$ methyl ester there was obtained 13-cis-$PGE_3$ methyl ester.

EXAMPLE 61

Preparation of the Enantiomer of 13-cis-15-epi-$PGE_3$ Methyl ester (XVI)

Following the procedure of Example 54 but substituting an equivalent amount of the enantiomer of 13-cis- 15-epi-PGF$_{3\alpha}$ methyl ester for the 13-dehydro-PGF$_{2\alpha}$ methyl ester there was obtained the enantiomer of 13-cis-15-epi-PGE$_3$ methyl ester.

EXAMPLE 62

Following the procedure set forth in Example 23 (b), but substituting equivalent amounts of (−)-(S)-3-methyl-3-t-butoxyoctyne and (−)-(S)-3-methyl-3-t-butoxy-cis-oct-5-ene-1-yne for (−)-(S)-3-butoxy-octyne, there is obtained the corresponding alane reagent.

The above reagents may be prepared by following the procedure set forth in Example 7 of my copending prior filed application Ser. No. 274,365, filed July 24, 1972, but substituting methyl pentyl ketone or methyl-cis-2-pentenyl ketone for cis-3-hexene-1-al; and following the subsequent Examples of said Application to obtain the desired final products.

EXAMPLE 63

13-Dehydro-15-epi-PGE$_2$ methyl ester may be acylated by treatment with an acyl halide, for example, acetyl chloride, in pyridine, to yield the corresponding acetylated derivative.

EXAMPLE 64

Preparation of 13-Dehydro-PGA$_2$ (XVIa)

A solution of 20 mg of 13-dehydro-PGE$_2$ (XIVa) in 2 ml of 0.5 N HCl in tetrahydrofuran-H$_2$O 1:1 was stirred vigorously at 25° for 72 hrs. The solution was then partly neutralized to pH 4 and extracted with ethyl acetate. The ethyl acetate extract was washed back once with brine dried over sodium sulfate and the solvent evaporated in vacuo. The residue consisted of 13.3 mg of 13-dehydro-PGA$_2$ (XVIa).

Following the procedure of the above example but substituting equivalent amounts of 13-dehydro-PGE$_3$ (XIVc), the enantiomer of 15-epi-13-dehydro-PGE$_2$ (XVa) or the enantiomer of 15-epi-13-dehydro-PGE$_3$ (XVc) for the 13-dehydro-PGE$_2$ there are obtained 13-dehydro-PGA$_3$ (XVIc), the enantiomer of 15-epi-PGA$_2$ (XVIIa) and the enantiomer of 15-epi-13-dehydro-PGA$_3$ (XVIIc), respectively.

EXAMPLE 65

Preparation of erythro-4-fluoro-1-octyne-3-ol AXIIa, R=n-pentyl) and threo-4-fluoro-1-octyne-3-ol AXIIIa, R=n-pentyl)

2-Fluorohexanal hydrate

A solution of ethyl 2-fluorocaproate (AX, R=n-pentyl) prepared in accordance with the method of Elkik and Assadi-Far, Compt. Rend. Series C, 262 (9) 763 (1966), (9.50 g, 58.6 mmol) in 45 ml of dry hexane was cooled under N$_2$ to −75° in a 300 ml round bottom flask equipped with a 50 ml pressure-equalized addition funnel. Into the funnel was injected through a rubber septum, a solution of diisobutyl aluminum hydride in 30 ml of hexane, prepared from 15 ml of 1.2 molar diisobutyl aluminum hydride in toluene by evaporating the toluene in vacuo and replacing it by hexane. After addition of the diisobutyl aluminum hydride solution over a 35 min period the mixture was stirred magnetically for 5 hr at −70°±3°. At the same temperature 75 ml of 10% HCl was then added dropwise, the dry ice-acetone bath removed and stirring continued until a homogeneous solution resulted. After saturation with NaCl the aqueous solution was extracted with 3 100 ml portions of CH$_2$Cl$_2$. The combined extracts were washed with saturated sodium chloride (3×25 ml) and dried over anhydrous MgSO$_4$. The solvent was removed in vacuo leaving a liquid residue which after distillation gave 6.04 g of 2-fluorohexanal hydrate (AXI, R=n-pentyl), bp 70°–80° at 167 mm. Various other side chains, i.e. Compounds AIII, wherein R=alkyl or alkenyl, may be prepared by variation of the Elkik and Assadi-Far procedure as is well recognized to the skilled worker.

Thus, in the preparation of Compounds AIII, R may be substituted by lower alkyl of 3–6 carbon atoms by lower alkenyl of from 3 to 6 carbon atoms or by aralkyl of from 7–9 carbon atoms merely by rearranging the configuration of the starting material.

(±)-Erythro and (±)-threo-4-fluoro-1-octyne-3-ol

Ethynyl magnesium bromide in tetrahydrofuran (THF) prepared from 4.0 g (164 mmol) Mg turnings and 20.4 g (187 mmol) ethyl bromide was placed in a 500 ml 3-neck round bottom flask equipped with a nagnetic stirrer and an addition funnel under an atmosphere of N$_2$ and cooled to 2°–3° with an ice bath. A solution of 2-fluorohexanal hydrate (4.70 g, 34.6 mmol) in 10 ml of dry THF was placed in the additional funnel and added dropwise to the Grignard reagent over 10 min at 2°–3° with stirring. The resulting gray heterohgeneous mixture was allowed to stir 1 hr under N$_2$ allowing the ice to melt. When the bath was removed the stirring was continued for another 20 min. The reaction mixture was withdrawn with a 50 ml syringe and injected rapidly into a vigorously stirred saturated solution of NH$_4$Cl in wafer maintained at ice bath temperature. The THF layer was separated, and the aqueous layer extracted with ether (3×50 ml). The combined THF-ether solutions were washed with brine (4×25 ml) and dried over anhydrous Na$_2$SO$_4$. After careful concentration on a rotary exaporator (bath temperature 20°) the residue (8.71 g) was distilled under reduced pressure through a Vigreux column with a vacuum jacket to give 3.87 g (78%) of (±)-erythro and (±)-threo-4-fluoro-1-octyne-3-ol as a colorless oil, bp 82.5°–85° at 10 mm. Analysis Calcd for C$_8$H$_{13}$OF. C, 66.63; H, 9.09; F, 13.18. Found: C, 66.69; H, 8.89; F, 13.61.

This material consists of an erythro-threo mixture in the ratio of 2.2:1.

Erythro and threo-4-Fluoro-1-octyne-3-ol hydrogen phthalate

A 50 ml pear shaped flask equipped with a spiral reflux condenser was charged with 0.576 g (4.0 mmol) of the above 2.2:1 mixture of erythro and threo-4-fluoro-1-octyne-3-ols. 0.592 g (4.0 mmol) of phthalic anhydride and 0.8 ml of dry pyridine. The mixture was refluxed for 2 hrs (oil bath temperature 115°–120°) cooled to room temperature and acidified to pH2 with 10% HCl with chilling in an ice bath. The acidified mixture was extracted with benzene (4×5 ml) and the combined layers washed with brine (4×2 ml) and dried over anhydrous Na$_2$SO$_4$. Removal of the solvent under reduced pressure gave 1.12 g (96%) of a yellow-brown viscous oil, which was induced to crystallization in 1 ml of hexane. After washing with another 2 ml of hexane a nearly colorless solid (0.630 g) mp 74.5°–78.5° was obtained. The hexane washings afforded 386 mg of an oil. The above solid after 2 crystallizations from CCl$_4$-hexane gave the erythro hydrogen phthalate (0.38 g), mp 82°–82.6° as colorless crystals (34% yield). An analytical sample was obtained after 3 crystallizations from etherhexane, mp 83°–84°.

Analysis Calcd for, $C_{16}H_{17}O_4F$. C, 65.74; H, 5.86; F, 6.50. Found: C, 65.58; H, 5.77; F, 6.22.

The oil from the hexane washings and the mother liquors from the above erythro isomer were combined and crystallized several times from $CCl_4$-hexane (1:3). This gave additional amounts of the erythro isomer, followed by the pure threo isomer, mp 79°–79.5°. After 2 crystallizations from ethyl acetate-hexane the sample was analyzed.

Found: C, 65.67; H, 5.92; F, 6.32.

Resolution of erythro- and threo-4-Fluoro-1-octyne-3-ol

Preparation of (3S, 4S)-4-fluoro-1-octyne-3-ol hydrogen phthalate (S)-α-phenethylamine salt To a solution o 292 mg of erythro-4-fluoro-1-octyne-3-ol hydrogen phthalate (0.1 mmol) in 2 ml of $CH_2Cl_2$ cooled in an ice water bath is added 121 mg (0.1 mmol) of (−)-(S)-α-phenethylamine. The mixture is allowed to warm to 25° and kept at that temperature for 20 min. The solvent is then evaporated under reduced pressure and the salt cooled in the refrigerator overnight which induced crystallization. Two crystallizations of this salt from ethyl acetate yields the pure (3S, 4S)-4-fluoro-1-octyne-3-ol hydrogen phthalate phenethylamine salt.

Preparation of (3S,4S)-4-fluoro-1-octyne-3-ol

The above (S)-α-phenethylamine salt is dissolved in 5 ml of 5% NaOH and the solution stored at 5°–10° for 30 min. The reaction mixture is cooled and extracted with six 10 ml portions of ether. The ether layer is washed with 0.5 N HCl (3×10 ml) until the pH reaches 1, followed by washes with 10 ml of brine, 2 ml of 5% sodium bicarbonate and again with 10 ml of brine. The solution is dried over magnesium sulfate and the ether carefully removed by fractional distillation. The residue constitutes pure (3S,4S)-4-fluoro-1-octyne-3-ol.

Preparation of (3S,4S)-3-t-butyloxy-4-fluoro-1-octyne

Isobutylene (7 ml) was condensed from a cylinder below −20° under $N_2$ and diluted with precooled 25 ml $CH_2Cl_2$. This solution was cooled to −60° and there was added 2.9 g (21 mmol) of (3S,4S)-4-fluoro-1-octyne-3-ol, in 15 ml of $CH_2Cl_2$, 0.70 ml of $BF_3$ etherate and 0.34 ml of anhydrous $H_3PO_4$, in the order given. The mixture was allowed to warm to 0°–15° and stirred for 40 min at that temperature. The resulting pale yellow solution was cooled again to −50° and poured into a vigorously stirred solution of saturated sodium bicarbonate (70 ml) kept cool in an ice water bath. The heterogeneous mixture was agitated vigorously until the organic layer became basic towards pH paper. The $CH_2Cl_2$ layer was separated, washed with water (40 ml ) and brine (30 ml) and dried over anhydrous $Na_2SO_4$. Concentration on a rotary evaporator afforded 9.87 g of a colorless oil which was chromatographed on 70 g of silica gel. Less polar impurities were eluted with hexane. Elution with pentane-ether 9:1 (100 ml) gave the crude t-butyloxy fluorooctyne, which on distillation under vacuum (bp 57° at 3–4 min) gave 3.69 g (91%) of pure material.

Analysis: Calcd for $C_{12}H_{21}OF$. C, 71,96; H, 10.57; F, 9.49. Found: C, 71.71; H, 10.48; F, 9.79.

When the above sequence of steps was applied to threo-4-fluoro-1-octyne-3-ol hydrogen phthalate there was obtained (3S,4R)-3-t-butyloxy-4-fluoro-1-octyne.

EXAMPLE 66

Preparation of the triol (Compound AIVd M is t-butyl, R=n-pentyl)

Into an oven-dried 50 ml 3-neck round bottom flask fitted with a septum, an addition funnel and a condenser topped with a nitrogen inlet injector, purged with nitrogen, was placed 1.3 g (6.5 mmol) of (3S,4S)-3-t-butyloxy-4-fluoro-1-octyne in 1.5 ml of dry toluene. To the ice-cooled mixture was added 3.82 ml (6.5 mmol) of 1.7 molar n-butyl-lithium in hexane dropwise over a 45 min period and the mixture stirred in the cold for another 15 min. To this solution was added 4.3 ml ((4.23 mmol) of 1.0 M methyl methoxy aluminum chloride via syringe and the resulting mixture stirred in the cold for 50 min. The slightly yellow solution was allowed to warm to room temperature and a solution of the epoxy diol starting material (Compound AII), 72 mg (0.5 mmol) in 1.6 ml of toluene was injected via syringe. The resulting mixture was heated at 35°±2° for 3¼ hrs. It was then cooled in an ice bath and saturated $Na_2SO_4$ was added until gas evolution ceased (approximately 2 ml). The mixture was stirred at 20 for 5 min then transferred to a 250 ml Erlenmeyer flask with 100 ml of ether. Anhydrous sodium sulfate was added and the mixture stirred for 10 min. The solid was filtered and thoroughly washed with ether. Evaporation of solvent gave 1.4 g of yellow oil. The above crude oil was chromatographed on 30 g of silica gel.

Elution of the column with pentane-ether 9:1 yielded 1.09 g of recovered (3S,4S)-3-t-butyloxy-4-fluoro-1-octyne which was purified by distillation. Further elution with pentane-ethyl acetate (1:4) containing 0.1% of pyriding eluted 76.6 mg of product (Compounds AIVd) (M=t-butyl, R=n-pentyl). In order to remove a by-product, from which hydrogen fluoride had been eliminated the crude product mixture was hydrolyzed with 2.5 ml of 0.03 N hydrogen chloride in acetonitrile-water (2:1) at room temperature for 16 hrs. The mixture was neutralized by adding solid sodium bicarbonate to pH 7 then saturated with solid sodium chloride and extracted with 4×3 ml of ether. The aqueous phase was treated with solid $Na_2SO_4$ and evaporated to dryness to furnish 69.5 mg of the triol (M=t-butyl, R=n-pentyl) and some ketonic by-product. These two products were separated by preparative thin layer chromatography on two 20×20 cm silica gel plates (2.5 ml thick) and the plates eluted 3 times with ethyl acetate. The top band was extracted with ethyl acetate to give 36.7 mg of the 16-fluoro-triol (M=t-butyl, R=n-pentyl). The band right below it on extraction with ethyl acetate yielded 6 mg of the ketonic by-product.

Following the above procedure but substituting the other enantiomeric diol epoxide (Compound AI) there are obtained the corresponding fluorinated triol (Compound AIVb).

Again applying the above procedure to the triol epoxides (Compounds AI and AII) but substituting the aluminum reagent prepared from (3S,4R)-3-t-butoxy-4-fluoro-1-octyne there are obtained the corresponding fluorinated triols (Compounds AIVa and AIVc, respectively).

EXAMPLE 67

Preparation of the 15-t-Butoxy lactone (Compound AVd)

Platinum dioxide (121 mg, Engelhart no. 46) was reduced with hydrogen at room temperature under atmospheric pressure in 11 ml of distilled water for 1¾ hr. The reaction vessel was then successively evacuated and filled with nitrogen (4 times) after which time oxygen was bubbled into the catalyst mixture for 5 min. A solution of 60 mg of the fluoro triol (Compound AIVd) from Example 2 in 5.4 ml of acetone-water 1:4 was added over a period of 2 min via an addition funnel and the funnel washed with 0.8 ml of acetone. The reaction flask was then placed in an oil bath at 57 and oxygen introduced directly into the heterogeneous mixture. After completion of the reaction (5⅜ hrs) the catalyst was filtered by suction through celite and the celite thoroughly washed with ethyl acetate. The aqueous layer was extracted 3 times with ethyl acetate and the combined ethyl acetate extracts successively washed with 5% HCl and saturated NaCl solution and then filtered with suction in vacuo gave the crude lactone (54.6 mg, 92% yield) which was purified by preparative thin layer chromotography (eluent ethyl acetate-hexane 5:1) to give 35 mg (59.1%) of pure lactone (Compound AVd).

When the above procedure was repeated employing the other diastereomeric 16-fluoro triols of Example 66 as reactants there were obtained the corresponding diastereomeric lactones, respectively (Compounds AV).

EXAMPLE 68

Preparation of the 16-fluoro hemi acetal (Compound AVId)

To a solution of 3.9 mg (0.0115 mmol) of the 16-fluoro lactone (Compound AVd) of Example 3 in 0.1 ml of toluene was added at −60° to −65° 0.031 mmol (26 ml) of a 1.2 M solution of diisobutylaluminum hydride in toluene. The reaction was complete after 1½ hr under nitrogen upon which the mixture was acidified with 5% hydrochloric acid and allowed to warm to room temperature. Solid anhydrous sodium sulfate in ethyl acetate was added, the moisture stirred vigorously and the solid salts removed by suction filtration. Removal of the solvent in vacuo gave the crude 16-fluoro hemiacetal (Compound VId) (4.6 mg) which was purified by tlc (elution with ethyl acetate) to give 2.7 mg (70%) of pure 16-fluoro hemiacetal (Compound AVId).

When the above procedure was repeated with the other diastereomeric 16-fluoro Iacetones of Example 67 above, there were obtained the corresponding diastereomeric hemiacetals (Compounds AVI) respectively.

EXAMPLE 69

Preparation of (15S,16S) 16-fluoro-13-dehydro-PGF$_2$a, (Compound AVIId) into a 2-neck round bottom flask, dried and flushed with nitrogen was placed 74.6 mg of a 45% NaH-oil suspension, which had been washed 3 times with dry hexane under nitrogen, followed by addition of 1 ml of dry dimethyl sulfoxide (freshly distilled over CaH$_2$ and stored over molecular sieves). The resulting temperature suspension was heated at a bath teperature of 70°–75° for 1 hr, the resulting grayish-green solution cooled to 25°, and 372 mg of 5-triphenylphosphoniovaleric acid bromide (dried under vacuum at 70° for 24 hr), dissolved in 1 ml of DMSO added slowly by syringe through a rubber septum. After 10 min. 0.11 ml of this red solution (0.0456 mmol) was withdrawn by syringe and added to 2.6 mg (0.0076 mmol) of the 16-fluoro-hemiacetal (Compound AVId) of Example 68 dissolved in 20 ml of DMSO under nitrogen. The mixture was heated at 55° for 2½ hr cooled in an ice bath and carefully acidified with 0.5% HCl to pH2. Additional brine was added and the solution extracted with 4×2 ml of ethyl acetate. The combined ethyl acetate extracts were washed with brine (1×2 ml+1×1 ml) and dried over Na$_2$SO$_4$. The crude product obtained by evaporation of the solvent in vacuo was triturated with 2 ml ether and 5 drops of ethyl acetate, seeded with triphenylphosphonic-valeric acid chloride and allowed to remain in the freezer overnight. Crystals of the unreacted acid were centrifuged and washed with ether (1×2 ml, 1×1 ml) and the ethyl acetate-ether solution concentrated in vacuo. The residue was dissolved in 1 ml ether, 2 drops of hexane were added and the mixture kept at −10° for 4 hr to precipitate more of the unreacted acid. The residue after removal of the ether-hexane was taken up in sodium carbonate solution (pH 9) and extracted 4 times with ether. The ether layers were back-washed with 3 drops saturated sodium carbonate in 0.5 ml of brine and finally brine and the ether layer containing triphenylphosphine oxide and other impurities discarded. The aqueous phase was acidified with 5% hydrochloric acid to pH 1 and extracted 4 times with ethyl acetate. The ethyl acetate extract was back-washed with brine (1 ml) dried over Na$_2$SO$_4$ and evaporated to dryness in vacuo leaving 2.9 mg of crude reaction product.

This material was dissolved in 100 microlites of CF$_4$COOH and 10 microlites of anisol at 0° and allowed to remain at that temperature for 1.5 hr. The trifluoroacetic acid and anisol were then removed in vacuo finally at 1 mm. The resulting residue was hydrolyzed with sodium carbonate (0.1 ml of ⅓ saturated solution) at 25 for ½ hr to remove esters of trifluoroacetic acid. The hydrolysis solution was then extracted with ether (3×1 ml) and the ether layer back-washed with sodium carbonate and brine (0.5 ml brine+3 drops saturated Na$_2$CO$_3$) and finally with brine (0.5 ml). The combined aqueous layers were then acidified with 5% hydrochloric acid to pH 1 saturated with sodium chloride and extracted with ethyl acetate (4×2 ml). The combined ethyl acetate extracts were again washed with brine (0.5 ml) and dried over Na$_2$SO$_4$. The bulk of the solvent was evaporated in vacuo and additional solvents added and evaporated to remove traces of trifluoroacetic acid. The residual product on purification by high pressure liquid chromatography on silica gel gave pure (15S,16S)-16-fluoro-13-dehydro-PGF$_2$a, (Compound AVIId).

Repeating the above procedure, but employing the other diastereomeric fluoro hemiacetals of Example 68 there were obtained the corresponding diastereomeric-16-fluoro-13-dehydroprostaglandins F$_2$a, (Compounds AVII) respectively.

EXAMPLE 70

Preparation of (15S,16S)-16-fluoro-13-dehydro-PGE$_2$ methyl ester (Compound AVIId, Q=CH$_3$)

To a solution of 20 mg of (15S,16S)-16-fluoro-13-dehydro-PGF$_2$ methyl ester (prepared from the compound of Example 69 with ethereal diazomethane containing 10% of methanol for 10 min at 0° followed by evaporation of the solvent) in 0.4 ml of dry acetone was added with stirring at −40° under nitrogen 0.8 ml of N-trimethylsilyldiethylamine. After 1 hr the reaction was quenched with 6 ml of dry methanol and the mixture allowed to warm to 25°. Evaporation to dryness under reduced pressure yielded as the major product the 11, 15-bis-trimethylsilyl derivative which was oxidized with Collins reagent in situ (prepared from 36 mg of chromium trioxide and 55 microlites of pyridine in 0.8 ml of $CH_2Cl_2$) for 5 min at 25° followed by desilylation with a mixture of 1 ml of methanol, 0.1 ml of water and 0.05 ml of acetic acid for 1 hr. High pressure liquid chromatography on silica gel afforded an elution with varying ratios of hexane and ethyl acetate 10 mg of (15S,16S)-16-fluoro-13-dehydro-$PGE_2$ methyl ester) (Compound AVIIId, Q=$CH_3$).

Applying the above procedure to the other diasteromeric fluoro-13-dehydro-prostaglandins $F_{2a}$, of Example 69 there are obtained the corresponding fluoro-13-dehydroprostaglandin $E_2$ methyl esters (Compounds AVIII).

EXAMPLE 71

Preparation of (15S,16S)-16-fluoro-13-dehydro-$PGA_2$ methyl ester (Compound AIXd, Q=$CH_3$)

A solution of 20 mg of (15S,16S)-16-fluoro-13-dehydro-$PGE_2$ methyl ester of Example 70 in 2 ml of 0.5 N HCl in tetrahydrofuran-$H_2O$ (1:1) was stirred vigorously at 25° for 72 hr. The solution was then partly neutralized to pH 4 and extracted with ethyl acetate. The ethyl acetate extract was washed back once with brine and the solvent evaporated in vacuo. The residue consists of 13.3 mg of (15S,16S)-16-fluoro-13-dehydro-$PGA_2$ methyl ester (Compound AIXd, Q=$CH_3$).

Following the above procedure but utilizing instead the other diastereomeric methyl esters of Example 70, there were obtained the corresponding 16-fluoro-$PGA_2$ derivatives (Compounds AIX).

It should be understood in the practice of this invention that in the preparation of the various compounds producable thereby, whenever a compound having free hydroxy groups is produced it may be further treated in accordance with methods well known in the art to provide the respective acyl and alkyl derivatives thereof. Thus, a compound of this invention having free hydroxy groups may be treated with a suitable acylating agent, such as those derived from hydrocarbon carboxylic acids of twelve carbon atoms or less to yield the desired acyloxy derivatives as is well known to the skilled worker. Likewise, such free hydroxy compounds may be treated with a suitable known alkylating agents to yield the respective alkoxy derivatives, and most preferably the lower alkyl-alkylating agents may be employed in the practice of this invention, to yield the desired lower-alkoxy derivatives.

The invention may be variously otherwise embodied within the scope of the appended claims.

What is claimed is:

1. An optically active compound of the formula:

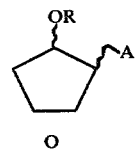

wherein A is $CH_2OH$, or

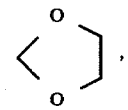

and R is hydrogen.

* * * * *